United States Patent [19]
Maclaren et al.

[11] Patent Number: 5,989,551
[45] Date of Patent: Nov. 23, 1999

[54] MATERIALS AND METHODS FOR DETECTION AND TREATMENT OF INSULIN-DEPENDENT DIABETES

[75] Inventors: Noel K. Maclaren, Gainesville, Fla.; Abner L. Notkins, McLean, Va.; Michael S. Lan, Rockville; Qing Li, Gaithersburg, both of Md.

[73] Assignees: The United States of America as represented by the Department of Health and Human Services, Washington, D.C.; The University of Florida, Gainesville, Fla.

[21] Appl. No.: 08/548,159

[22] Filed: Oct. 25, 1995

[51] Int. Cl.$^6$ .......................... A61K 39/00; A61K 38/00
[52] U.S. Cl. ...................... 424/185.1; 530/324; 530/350; 435/325
[58] Field of Search ........................... 435/7.1, 7.9, 69.1, 435/325; 424/184.1, 133.1, 185.1; 530/350, 303, 305, 324; 514/866

[56] References Cited

U.S. PATENT DOCUMENTS 5,200,318 4/1993 Rabin et al. ........................... 435/7.21

OTHER PUBLICATIONS

Ezio Bonifacio et al., Journal of Immunology., vol. 155., No. 11., pp. 5419–5426., Dec. 1995.

Lu et al. Identification of a Second Transmembrane Protein Tyrosine Phosphatase, IA–2β, as an Autoantigen in insulin–dependent diabetes mellitus . . . *Medical Sciences* 93:2307–2311, Mar. 1996.

Atkinson, M., N.K. Maclaren (1994) "Mechanisms of Disease" New England Journal of Medicine 331:1428–1436.

Maclaren, N.K., W.J. Riley (1985) "Thyroid, Gastric, and Adrenal Autoimmunities Associated with Insulin–Dependent Diabetes Mellitus" Diabetes Care 8(Sup. 1):34–38.

Lendrum, R., G. Walker, D.R. Gamble (1975) "Islet–Cell Antibodies in Juvenile Diabetes Mellitus of Recent Onset" The Lancet 1:880–882.

Maclaren, N.K., S.–W. Huang, J. Fogh (1975) "Antibody to Cultured Human Insulinoma Cells in Insulin–Depdnent Diabetes" The Lancet 1:997–1000.

Kaufman, D.L. et al. (1992) "Autoimmunity to Two Forms of Glutamate Decarboxylase in Insulin–dependent Diabetes Mellitus" J. Clin. Invest. 89:283–292.

Atkinson, M.A. et al. (1992) "Response of peripheral–blood monoclear cells to glutamate decarboxylase in insulin–dependent diabetes" The Lancet 339:458–459.

Harrison, L.C. et al. (1993) "Inverse relation between humoral and cellular immunity to glutamic acid decarboxylase in subjects at risk of insulin–dependent diabetes" The Lancet 341:1365–1369.

Atkonsin, M.A. et al. (1994) "Cellular Immunity to a Determinant Common to Glutamate Decarboxylase and Coxsackie Virus in Insulin–dependent Diabetes" J. Clin. Invest. 94:2125–2129.

Maclaren, N.K. (1988) "How, When, and Why to Predict IDDM" Diabetes 37(12):1591–1594.

Muir, A. et al. (1993) "Intervention Therapies for Insulin–Dependent Diabetes" Autoimmunity 16:301–310.

Atkinson, M.A. et al. (1986) "Are Insulin Autoantibodies Markers for Insulin–Dependent Diabetes Mellitus?" Diabetes 35:894–898.

Riley, W.J. et al. (1990) "A Prospective Study of the Development of Diabetes in RElatives of Patients with Insulin–Dependent Diabetes" New England Journal of Medicine 323:1167–1172.

Schatz, D. et al. (1994) "Islet Cell Antibodies Predict Insulin–dependent Diabetes in United States School Age Childredn as Powerfully as in Unaffected Relatives", J. Clin. Invest. 93:2403–2407.

Krischer, J.P. et al. (1993) "Insulin and Islet Cell Autoantibodies as Time–Dependent Covariates in the Development of Insulin–Dependent Diabetes: A Prospective Study in Relatives" Journal of Clinical Endocrinology and Metabolism 77(3):743–749.

Schott, M. et al. (1994) "GAD$_{65}$ Autoantibodies Increase the Predictability but not the Sensitivity of Islet Cell and Insulin Autoantibodies for Developing Insulin Dependent Diabetes Mellitus" Journal of Autoimmunity 7:865–872.

Atkinson, M.A., N.K. Maclaren (1993) "Islet Cell Autoantigens in Insulin–dependent Diabetes" J. Clin. Invest. 92:1608–1616.

Genovese, S. et al. (1992) "Distinct cytoplasmic islet cell antibodies with different risks for Type 1 (insulin–dependent) diabetes mellitus" Diabetologia 35:385–388.

Atkinson, M.A. et al. (1993) "Islet Cell Cytoplasmic Autoantibody Reactivity to Glutamate Decarboxylase in Insulin–dependent Diabetes" J. Clin. Invest. 91:350–356.

Payton, M.A. et al. (1995) "Relationship of the 37,000–and 40,000–$M_r$ Tryptic Fragments of Islet Antigens in Insulin–dependent Diabetes to the Protein Tyrosine Phosphatase–like Moleculae IA–2 (ICA512)" J. Clin. Invest. 96:1506–1511.

Lan, M.S. et al. (1994) "Molecular Cloning and Identification of a Receptor–Type Protein Tyrosine Phosphatase, IA–2, from Human Insulinoma" DNA and Cell Biology 13(5):505–514.

Baekkeskov, B. et al. (1990) "Identification of the 64F autoantigen in insulin–dependent diabetes as the GABA–synthesizing enzyme glutamic acid decarboxylase" Nature 347:151–156.

Maron, R. et al. (1983) "Autoantibodies to the insulin receptor in juvenile onset insulin–dependent diabetes" Nature 303:817–818.

(List continued on next page.)

*Primary Examiner*—Ponnathapura Achutamurthy
*Assistant Examiner*—P. Ponnaluri
*Attorney, Agent, or Firm*—Needle & Rosenberg, P.C.

[57] ABSTRACT

The method and compositions of this invention provide an effective and reliable substitute for the currently employed ICA assay for diabetes. By providing a method for detecting autoantibodies to GAD$_{65}$, IA-2 and a previously unidentified antigen termed IA-2β herein, the method provides a chemical assay which has improved reliability. In addition, these antigens may be employed in therapeutic regimens aimed at achieving amelioration of the clinical condition.

6 Claims, 7 Drawing Sheets

OTHER PUBLICATIONS

Palmer, J.P. et al. (1983) "Insulin Antibodies in Insulin–Dependent Diabetics Before Insulin Treatment" Science 222:1337–1339.

Atkinson, M.A., N.K. Maclaren (1988) "Autoantibodies in Nonobese Diabetic Mice Immunoprecipitate 64,000–$M_r$ Islet Antigen" Diabetes 37(11):1587–1590.

Atkinson, M.A., N.K. Maclaren (1990) "What Causes Diabetes?" Scientific American 262(7):62–71.

Baekkeskov, S. et al. (1982) "Autoantibodies in newly diagnosed diabetic children immunoprecipitate human pancreatic islet cell proteins" Nature 298:167–169.

ATkinson, M.A. et al. (1990) "64,000 $M_r$ autoantibodies as predictors of insulin–dependent diabetes" The Lancet 335:1357–1360.

Baekkeskov, S. et al. (1982) "Antuantibodies to a 64–Kilodalton Islet Cell Protein Precede the Onset of Spontaneous Diabetes in the BB Rat" Science 224:1348–1350.

Rabin, D.A. et al. (1992) "An ELISA sandwich capture assay fro recombinant fusion proteins containing glutathion-s–S–transferase" Jouranl of Immunological Methods 156:101–105.

Rabin, D.A. et al. (1992) "Cloning and Expression of IDDM–Specific Human Autoantigens" Diabetes 41:183–186.

Rabin, D.A. et al. (1994) "Islet Cell Antigen 512 is a Diabetes–Specific Islet Autoantigen Related to Protein Tyrosine Phosphatases" Journal of Immunology 152:3183–3188.

Lu, J. et al. (1994) "Isolation, Sequence and Expression of a Novel Mouse Brain cD mIA–2, and its Relatedness to Members of the Protein Tyrosine Phosphatase Family" Biochem. Biophys. Res. Commun. 204:930–936.

```
IA-2β  EFGTRPPPPGDAKDSPSMDDDTLLQSLLKDLPQNSEVDPLGPLKEEKADS      50
       :||.|....|....|. :: : |..    ..| .|. .::  | ....:|
IA-2   QFGSRDGSRGSESSSGVVGVGHLSKAEGPALFSRSASKAI...LGTHSGHS     260

VAGAIQSDPAEGSQES..................HGTGAEGQPREQTDA      81
       .:: ....||:  |:|                      ...:..: : .::
       FGDLTGPSPAQLFQDSGLLYMAQELPVPGRARAPRLPENGGNRAEDSSEG     310

PETMLQDHRLSDDPVYKEVNRLSFQ.LGDLLKDYGSPLLPEGP.......     123
       .|. : : |  ...|. .   ||:| |..:| :|| .| . .|
       HEEEVLGGRGEKSPPQAAQPELSLQRLTAVLAGYGVELRQLTPEQFSTLL     360

.LLEKSSREEMKKLEQPEEVLSSE........EETAGVEHVRSRTYSKDL     164
       |::  .::. :.||.: :| :.:         : ....| :... . .::
       TLMQLLPKGTGRNLEGAVNVGGADVKKTIQQMQRGDPAEALPPTPSLPGY     410

FERKPNSEPQPRRLEDQFQNRAPELWEDEESLKLAAQGPPSGGLQLEV..     212
       :. .|.|.. .. |...|.:..:. .. :|  | ...| | . | .|
       LTASPASSEVQQVLSPGFPEPPHTPSPLGSSSVLLEKKSPLGQSQPTVVG     460

....QPSEEQQGYILTGNNPLSPEKGKQLMDQVAHILRVPSSFFADIKVL     258
       .||.|: |||:|:..|||    | .|:: :|. :::.|: | :|.|:
       RPSARPSAEEYGYIVTDQKPLSLVAGVRLLEILAEHVHMSSGSFINISVV     510

GPAVTFKVSANIQNMTTADVIKAAADNKDQLEKATGLTILQSGIRPKGK.     307
       ||||||::. | ||:. |||...|:  |.:||  .||| |||.|: .::.
       GPAVTFRIRHNEQNLSLADVTQQAGLVKSELEAQTGLQILQTGVGQREEA     560
                                      TM
       HKLLPHQEEQEDSTK┌FILLTFLSIACILGVLLASSLA┐YCLRHNSHYKLKD    357
       .:||:|...  .. :│:|||::.:|.: |:|:| .:|.│|.:||:|: : |:
       AEVLPRQAHGISPMR└SVLLTLVALAGVAGLLVALAVA┘LCMRHHSRQRDKE   610

KLSGLGADPS.ADATEAYQELCRQRMAVRPQ.DRSEG.PHTSRINSVSSQ     404
       :|.:||::.. :|.| .||:||||:||.:.  :|.|| |..||:.|||||
       RLAALGPEGAHGDTTFEYQDLCRQHMATKSLFNRAEGQPEPSRVSSVSSQ     660

FSDGPMPSPSARSSTSSWSEEPVQSNMDISTGHMILAYMEDHLKNKNRLE     454
       |||:: :|||.:||..||:|||.|.|.||||||||||||||||:|::||.
       FSDAAQASPSSHSSSPSWCEEPAQANMDISTGHMILAYMEDHLRNRDRLA     710

KEWEALCAYQAEPNSSLVAQREENAPKNRSLAVLTYDHSRILLKSQNSHG     504
       |||:|||||||||.: .|| |.| .|||   ..|.|||.|| ||  :.|.:
       KEWQALCAYQAEPNTCAAAQDESNIKKNRHPDFLPYDHARIKLKVESSPS     760
```

FIG.1A

```
SSDYINASPIMDHDPRNPAYIATQGPLPATVADFWQMVWESGCAVIVMLT    554
.|||||||||::||||  ||||||||||.  |:|||||||||||.||||||
RSDYINASPIIEHDPRMPAYIATQGPLSHTIADFWQMVWESGCTVIVMLT    810

PLSENGVRQCHHYWPDEGSNLYHVYEVNLVSEHIWCQDFLVRSFYLKNLQ    604
|| |:||:||.:|||||||.|||||||||||||||:||||||||||||
PLVEDGVKQCDRYWPDEGSSLYHVYEVNLVSEHIWCEDFLVRSFYLKNLQ    860

TNETRTVTQFHFLSWYDQGVPSSTRSLLDFRRKVNKCYRGRSCPII VHCS   654
|.||||:||||||||  .:|.|.|||.||||||||||||||||||| ||||
TQETRTLTQFHFLSWPAEGTPASTRPLLDFRRKVNKCYRGRSCPII VHCS   910

DGAGRSG TYVLIDMVLNKMAKGAKEIDIAATLEHLRDQRPGMVQTKEQFE   704
|||||.| ||:|||||||:||||.|||||||||||:||||||:|..|:|||
DGAGRTG TYILIDMVLNRMAKGVKEIDIAATLEHVRDQRPGLVRSKDQFE   960

FALTAVAEEVNAILKALPQ                                   723
|||||||||||||||||||
FALTAVAEEVNAILKALPQ                                   979
```

FIG.1B

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 969 amino acids
      (B) TYPE: amino acid
      (C) STRANDEDNESS: single
      (D) TOPOLOGY: linear (ii) MOLECULE TYPE: protein (vi) ORIGINAL SOURCE:
    (C) INDIVIDUAL ISOLATE: Human IL-2 Beta Protein (shorter version)

(xi) SEQUENCE DESCRIPTION: SEQ ID NO:1:

```
Met Gly Pro Pro Leu Pro Leu Leu Leu Leu Leu Leu Leu Leu Pro
1               5                   10                  15

Pro Arg Val Leu Pro Ala Ala Pro Ser Ser Val Pro Arg Gly Arg Gln
            20              25              30

Leu Pro Gly Arg Leu Asp Gly Val Phe Gly Arg Cys Gln Lys Val Pro
        35              40              45

Ala Met Asp Phe Tyr Arg Tyr Glu Val Ser Pro Val Ala Leu Gln Arg
50              55                  60

Leu Arg Val Ala Leu Gln Lys Leu Ser Gly Thr Gly Phe Thr Trp Gln
65              70              75                  80

Asp Asp Tyr Thr Gln Tyr Val Met Asp Gln Glu Leu Ala Asp Leu Pro
                85              90                  95

Lys Thr Tyr Leu Arg Arg Pro Glu Ala Ser Ser Pro Ala Arg Pro Ser
            100             105             110

Lys His Ser Val Gly Ser Glu Arg Arg Tyr Ser Arg Glu Gly Gly Ala
        115             120             125

Ala Leu Ala Asn Ala Leu Arg Arg His Leu Pro Phe Leu Glu Ala Leu
130             135             140

Ser Gln Ala Pro Ala Ser Asp Val Leu Ala Arg Thr His Thr Ala Gln
145             150             155             160

Asp Arg Pro Pro Ala Glu Gly Asp Asp Arg Phe Ser Glu Ser Ile Leu
                165             170             175

Thr Tyr Val Ala His Thr Ser Ala Leu Thr Tyr Pro Pro Gly Pro Arg
            180             185             190

Thr Gln Leu His Glu Asp Leu Leu Pro Arg Thr Leu Gly Gln Leu Gln
        195             200             205

Pro Asp Glu Leu Ser Pro Lys Val Asp Ser Gly Val Asp Arg His His
210             215             220

Leu Met Ala Ala Leu Ser Ala Tyr Ala Ala Gln Arg Pro Pro Ala Pro
225             230             235             240

Pro Gly Glu Gly Ser Leu Glu Pro Gln Tyr Leu Leu Arg Ala Pro Ser
                245             250             255

Arg Met Pro Arg Pro Leu Leu Ala Pro Ala Pro Gln Lys Trp Pro
            260             265             270

Ser Pro Leu Gly Asp Ser Glu Asp Pro Ser Ser Thr Gly Asp Gly Ala
        275             280             285

Arg Ile His Thr Leu Leu Lys Asp Leu Gln Arg Gln Pro Ala Glu Val
290             295             300

Arg Gly Leu Ser Gly Leu Glu Leu Asp Gly Met Ala Glu Leu Met Ala
305             310             315             320

Gly Leu Met Gln Gly Val Asp His Gly Val Ala Arg Gly Ser Pro Gly
                325             330             335

Arg Ala Ala Leu Gly Glu Ser Gly Glu Gln Ala Asp Gly Pro Lys Ala
            340             345             350

Thr Leu Arg Gly Asp Ser Phe Pro Asp Asp Gly Val Gln Asp Asp Asp
        355             360             365

Asp Arg Leu Tyr Gln Glu Val His Arg Leu Ser Ala Thr Leu Gly Gly
370             375             380
```

```
Leu Leu Gln Asp His Gly Ser Arg Leu Leu Pro Gly Ala Leu Pro Phe
385                 390                 395                 400

Ala Arg Pro Leu Asp Met Glu Arg Lys Lys Ser Glu His Pro Glu Ser
            405                 410                 415

Ser Leu Ser Ser Glu Glu Glu Thr Ala Gly Val Glu Asn Val Lys Ser
        420                 425                 430

Gln Thr Tyr Ser Lys Asp Leu Leu Gly Gln Gln Pro His Ser Glu Pro
        435                 440                 445

Gly Ala Ala Phe Gly Glu Leu Gln Asn Gln Met Pro Gly Pro Ser
450                 455                 460

Lys Glu Glu Gln Ser Leu Pro Ala Gly Ala Gln Glu Ala Leu Ser Asp
465                 470                 475                 480

Gly Leu Gln Leu Glu Val Gln Pro Ser Glu Glu Ala Arg Gly Tyr
                485                 490                 495

Ile Val Thr Asp Arg Glu Val Leu Gly Pro Ala Val Thr Phe Lys Val
            500                 505                 510

Ser Ala Asn Val Gln Asn Val Thr Thr Glu Asp Val Glu Lys Ala Thr
            515                 520                 525

Val Asp Asn Lys Asp Lys Leu Glu Glu Thr Ser Gly Leu Lys Ile Leu
    530                 535                 540

Gln Thr Gly Val Gly Ser Lys Ser Lys Leu Lys Phe Leu Pro Pro Gln
545                 550                 555                 560

Ala Glu Gln Glu Asp Ser Thr Lys Phe Ile Ala Leu Thr Leu Val Ser
                565                 570                 575

Leu Ala Cys Ile Leu Gly Val Leu Leu Ala Ser Gly Leu Ile Tyr Cys
            580                 585                 590

Leu Arg His Ser Ser Gln His Arg Leu Lys Glu Lys Leu Ser Gly Leu
        595                 600                 605

Gly Gly Asp Pro Gly Ala Asp Ala Thr Ala Ala Tyr Gln Glu Leu Cys
610                 615                 620

Arg Gln Arg Met Ala Thr Arg Pro Pro Asp Arg Pro Glu Gly Pro His
625                 630                 635                 640

Thr Ser Arg Ile Ser Ser Val Ser Ser Gln Phe Ser Asp Gly Pro Ile
            645                 650                 655

Pro Ser Pro Ser Ala Arg Ser Ser Ala Ser Ser Trp Ser Glu Glu Pro
            660                 665                 670

Val Gln Ser Asn Met Asp Ile Ser Thr Gly His Met Ile Leu Ser Tyr
    675                 680                 685

Met Glu Asp His Leu Lys Asn Lys Asn Arg Leu Glu Lys Glu Trp Glu
690                 695                 700

Ala Leu Cys Ala Tyr Gln Ala Glu Pro Asn Ser Ser Phe Val Ala Gln
705                 710                 715                 720

Arg Glu Glu Asn Val Pro Lys Asn Arg Ser Leu Ala Val Leu Thr Tyr
            725                 730                 735

Asp His Ser Arg Val Leu Leu Lys Ala Glu Asn Ser His Ser His Ser
        740                 745                 750

Asp Tyr Ile Asn Ala Ser Pro Ile Met Asp His Asp Pro Arg Asn Pro
        755                 760                 765

Ala Tyr Ile Ala Thr Gln Gly Pro Leu Pro Ala Thr Val Ala Asp Phe
    770                 775                 780

Trp Gln Met Val Trp Glu Ser Gly Cys Val Val Ile Val Met Leu Thr
785                 790                 795                 800

Pro Leu Ala Glu Asn Gly Val Arg Gln Cys Tyr His Tyr Trp Pro Asp
                805                 810                 815
```

```
        Glu Gly Ser Asn Leu Tyr His Ile Tyr Glu Val Asn Leu Val Ser Glu
                    820                 825                 830

His Ile Trp Cys Glu Asp Phe Leu Val Arg Ser Phe Tyr Leu Lys Asn
                    835                 840                 845

Leu Gln Thr Asn Glu Thr Arg Thr Val Thr Gln Phe His Phe Leu Ser
                    850                 855                 860

Trp Tyr Asp Arg Gly Val Pro Ser Ser Ser Arg Ser Leu Leu Asp Phe
        865                 870                 875                 880

Arg Arg Lys Val Asn Lys Cys Tyr Arg Gly Arg Ser Cys Pro Ile Ile
                    885                 890                 895

Val His Cys Ser Asp Gly Ala Gly Arg Ser Gly Thr Tyr Val Leu Ile
                    900                 905                 910

Asp Met Val Leu Asn Lys Met Ala Lys Gly Ala Lys Glu Ile Asp Ile
                    915                 920                 925

Ala Ala Thr Leu Glu His Leu Arg Asp Gln Arg Pro Gly Met Val Gln
                    930                 935                 940

Thr Lys Glu Gln Phe Glu Phe Ala Leu Thr Ala Val Ala Glu Glu Val
        945                 950                 955                 960

Asn Ala Ile Leu Lys Ala Leu Pro Gln
                    965
```

(2) INFORMATION FOR SEQ ID NO:2:

(i) SEQUENCE CHARACTERISTICS:
        (A) LENGTH: 2943 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (C) INDIVIDUAL ISOLATE: Human IL-2 Beta cDNA (shorter
            version)

(xi) SEQUENCE DESCRIPTION: SEQ ID NO:2:

```
CAGGCGGCGG GGATGGGGCC GCCGCTCCCG CTGCTGCTGC TGCTACTGCT GCTGCTGCCG      60

CCACGCGTCC TGCCTGCCGC CCCTTCGTCC GTCCCCCGCG GCCGGCAGCT CCCGGGGCGT     120

CTGGATGGAG TGTTTGGAAG GTGCCAGAAG GTTCCGGCAA TGGACTTTTA CCGCTACGAG     180

GTGTCGCCCG TGGCCCTGCA GCGCCTGCGC GTGGCGTTGC AGAAGCTTTC CGGCACAGGT     240

TTCACGTGGC AGGATGACTA TACTCAGTAT GTGATGGACC AGGAACTTGC AGACCTCCCG     300

AAAACCTACC TGAGGCGTCC TGAAGCATCC AGCCCAGCCA GGCCCTCAAA ACACAGCGTT     360

GGCAGCGAGA GGAGGTACAG TCGGGAGGGC GGTGCTGCCC TGGCCAACGC CCTCCGACGC     420

CACCTGCCCT TCCTGGAGGC CCTGTCCCAG GCCCCAGCCT CAGACGTGCT CGCCAGGACC     480

CATACGGCGC AGGACAGACC CCCCGCTGAG GGTGATGACC GCTTCTCCGA GAGCATCCTG     540

ACCTATGTGG CCCACACGTC TGCGCTGACC TACCCTCCCG GGCCCCGGAC CCAGCTCCAC     600

GAGGACCTCC TGCCACGGAC CCTCGGCCAG CTCCAGCCAG ATGAGCTCAG CCCTAAGGTG     660

GACAGTGGTG TGGACAGACA CCATCTGATG GCGGCCCTCA GTGCCTATGC TGCCCAGAGG     720

CCCCCAGCTC CCCCCGGGGA GGGCAGCCTG GAGCCACAGT ACCTTCTGCG TGCACCCTCA     780

AGAATGCCCA GGCCTTTGCT GGCACCAGCC GCCCCCCAGA AGTGGCCTTC ACCTCTGGGA     840

GATTCCGAAG ACCCCTCTAG CACAGGCGAT GGAGCACGGA TTCATACCCT CCTGAAGGAC     900

CTGCAGAGGC AGCCGGCTGA GGTGAGGGGC CTGAGTGGCC TGGAGCTGGA CGGCATGGCT     960
```

-continued

```
GAGCTGATGG CTGGCCTGAT GCAAGGCGTG GACCATGGAG TAGCTCGAGG CAGCCCTGGG    1020

AGAGCGGCCC TGGGAGAGTC TGGAGAACAG GCGGATGGCC CCAAGGCCAC CCTCCGTGGA    1080

GACAGCTTTC CAGATGACGG AGTGCAGGAC GACGATGATA GACTTTACCA AGAGGTCCAT    1140

CGTCTGAGTG CCACACTCGG GGGCCTCCTG CAGGACCACG GGTCTCGACT CTTACCTGGA    1200

GCCCTCCCCT TTGCAAGGCC CCTCGACATG GAGAGGAAGA AGTCCGAGCA CCCTGAGTCT    1260

TCCCTGTCTT CAGAAGAGGA GACTGCCGGA GTGGAGAACG TCAAGAGCCA GACGTATTCC    1320

AAAGATCTGC TGGGGCAGCA GCCGCATTCG GAGCCCGGGG CCGCTGCGTT TGGGGAGCTC    1380

CAAAACCAGA TGCCTGGGCC CTCGAAGGAG GAGCAGAGCC TTCCAGCGGG TGCTCAGGAG    1440

GCCCTCAGCG ACGGCCTGCA ATTGGAGGTC CAGCCTTCCG AGGAAGAGGC GCGGGGCTAC    1500

ATCGTGACAG ACAGAGAGGT TCTCGGACCA GCAGTGACCT TCAAAGTGAG CGCCAATGTC    1560

CAAAACGTGA CCACTGAGGA TGTGGAGAAG GCCACAGTTG ACAACAAAGA CAAACTGGAG    1620

GAAACCTCTG GACTGAAAAT TCTTCAAACC GGAGTCGGGT CGAAAAGCAA ACTCAAGTTC    1680

CTGCCTCCTC AGGCGGAGCA AGAAGACTCC ACCAAGTTCA TCGCGCTCAC CCTGGTCTCC    1740

CTCGCCTGCA TCCTGGGCGT CCTCCTGGCC TCTGGCCTCA TCTACTGCCT CCGCCATAGC    1800

TCTCAGCACA GGCTGAAGGA GAAGCTCTCG GGACTAGGGG GCGACCCAGG TGCAGATGCC    1860

ACTGCCGCCT ACCAGGAGCT GTGCCGCCAG CGTATGGCCA CGCGGCCACC AGACCGACCT    1920

GAGGGCCCGC ACACGTCACG CATCAGCAGC GTCTCATCCC AGTTCAGCGA CGGGCCGATC    1980

CCCAGCCCCT CCGCACGCAG CAGCGCCTCA TCCTGGTCCG AGGAGCCTGT GCAGTCCAAC    2040

ATGGACATCT CCACCGGCCA CATGATCCTG TCCTACATGG AGGACCACCT GAAGAACAAG    2100

AACCGGCTGG AGAAGGAGTG GGAAGCGCTG TGCGCCTACC AGGCGGAGCC CAACAGCTCG    2160

TTCGTGGCCC AGAGGGAGGA GAACGTGCCC AAGAACCGCT CCCTGGCCGT GCTGACCTAT    2220

GACCACTCCC GGGTCCTGCT GAAGGCGGAG AACAGCCACA GCCACTCAGA CTACATCAAC    2280

GCTAGCCCCA TCATGGATCA CGACCCGAGG AACCCCGCGT ACATCGCCAC CCAGGGACCG    2340

CTGCCCGCCA CCGTGGCTGA CTTTTGGCAG ATGGTGTGGG AGAGCGGCTG CGTGGTGATC    2400

GTCATGCTGA CACCCCTCGC GGAGAACGGC GTCCGGCAGT GCTACCACTA CTGGCCGGAT    2460

GAAGGCTCCA ATCTCTACCA CATCTATGAG GTGAACCTGG TCTCCGAGCA CATCTGGTGT    2520

GAGGACTTCC TGGTGAGGAG CTTCTATCTG AAGAACCTGC AGACCAACGA GACGCGCACC    2580

GTGACGCAGT TCCACTTCCT GAGTTGGTAT GACCGAGGAG TCCCTTCCTC CTCAAGGTCC    2640

CTCCTGGACT TCCGCAGAAA AGTAAACAAG TGCTACAGGG GCCGTTCTTG TCCAATAATT    2700

GTTCATTGCA GTGACGGTGC AGGCCGGAGC GGCACCTACG TCCTGATCGA CATGGTTCTC    2760

AACAAGATGG CCAAAGGTGC TAAAGAGATT GATATCGCAG CAACCCTGGA GCACTTGAGG    2820

GACCAGAGAC CCGGCATGGT CCAGACGAAG GAGCAGTTTG AGTTCGCGCT GACAGCCGTG    2880

GCTGAGGAGG TGAACGCCAT CCTCAAGGCC CTTCCCCAGT GAGCGGCAGC CTCAGGGGCC    2940

TCG                                                                 2943
```

(2) INFORMATION FOR SEQ ID NO:3:

(i) SEQUENCE CHARACTERISTICS:
        (A) LENGTH: 986 amino acids
        (B) TYPE: amino acid
        (C) STRANDEDNESS: single
        (D) TOPOLOGY: linear (ii) MOLECULE TYPE: protein (vi) ORIGINAL SOURCE:

(C) INDIVIDUAL ISOLATE: Human IL-2 Beta Protein (longer version)

(xi) SEQUENCE DESCRIPTION: SEQ ID NO:3:

```
Met Gly Pro Pro Leu Pro Leu Leu Leu Leu Leu Leu Leu Leu Pro
1               5                   10                  15

Pro Arg Val Leu Pro Ala Ala Pro Ser Ser Val Pro Arg Gly Arg Gln
            20                  25                  30

Leu Pro Gly Arg Leu Gly Cys Leu Leu Glu Glu Gly Leu Cys Gly Ala
                35                  40                  45

Ser Glu Ala Cys Val Asn Asp Gly Val Phe Gly Arg Cys Gln Lys Val
    50                  55                  60

Pro Ala Met Asp Phe Tyr Arg Tyr Glu Val Ser Pro Val Ala Leu Gln
65                  70                  75                  80

Arg Leu Arg Val Ala Leu Gln Lys Leu Ser Gly Thr Gly Phe Thr Trp
                85                  90                  95

Gln Asp Asp Tyr Thr Gln Tyr Val Met Asp Gln Glu Leu Ala Asp Leu
                100                 105                 110

Pro Lys Thr Tyr Leu Arg Arg Pro Glu Ala Ser Ser Pro Ala Arg Pro
            115                 120                 125

Ser Lys His Ser Val Gly Ser Glu Arg Arg Tyr Ser Arg Glu Gly Gly
130                 135                 140

Ala Ala Leu Ala Asn Ala Leu Arg Arg His Leu Pro Phe Leu Glu Ala
145                 150                 155                 160

Leu Ser Gln Ala Pro Ala Ser Asp Val Leu Ala Arg Thr His Thr Ala
                165                 170                 175

Gln Asp Arg Pro Pro Ala Glu Gly Asp Asp Arg Phe Ser Glu Ser Ile
                180                 185                 190

Leu Thr Tyr Val Ala His Thr Ser Ala Leu Thr Tyr Pro Pro Gly Pro
            195                 200                 205

Arg Thr Gln Leu His Glu Asp Leu Leu Pro Arg Thr Leu Gly Gln Leu
210                 215                 220

Gln Pro Asp Glu Leu Ser Pro Lys Val Asp Ser Gly Val Asp Arg His
225                 230                 235                 240

His Leu Met Ala Ala Leu Ser Ala Tyr Ala Ala Gln Arg Pro Pro Ala
                245                 250                 255

Pro Pro Gly Glu Gly Ser Leu Glu Pro Gln Tyr Leu Leu Arg Ala Pro
            260                 265                 270

Ser Arg Met Pro Arg Pro Leu Leu Ala Pro Ala Pro Gln Lys Trp
            275                 280                 285

Pro Ser Pro Leu Gly Asp Ser Glu Asp Pro Ser Ser Thr Gly Asp Gly
290                 295                 300

Ala Arg Ile His Thr Leu Leu Lys Asp Leu Gln Arg Gln Pro Ala Glu
305                 310                 315                 320

Val Arg Gly Leu Ser Gly Leu Glu Leu Asp Gly Met Ala Glu Leu Met
                325                 330                 335

Ala Gly Leu Met Gln Gly Val Asp His Gly Val Ala Arg Gly Ser Pro
                340                 345                 350

Gly Arg Ala Ala Leu Gly Glu Ser Gly Glu Gln Ala Asp Gly Pro Lys
                355                 360                 365

Ala Thr Leu Arg Gly Asp Ser Phe Pro Asp Asp Gly Val Gln Asp Asp
370                 375                 380

Asp Asp Arg Leu Tyr Gln Glu Val His Arg Leu Ser Ala Thr Leu Gly
385                 390                 395                 400
```

```
Gly Leu Leu Gln Asp His Gly Ser Arg Leu Leu Pro Gly Ala Leu Pro
                405                 410                 415

Phe Ala Arg Pro Leu Asp Met Glu Arg Lys Lys Ser Glu His Pro Glu
            420                 425                 430

Ser Ser Leu Ser Ser Glu Glu Thr Ala Gly Val Glu Asn Val Lys
        435                 440                 445

Ser Gln Thr Tyr Ser Lys Asp Leu Leu Gly Gln Gln Pro His Ser Glu
450                 455                 460

Pro Gly Ala Ala Ala Phe Gly Glu Leu Gln Asn Gln Met Pro Gly Pro
465                 470                 475                 480

Ser Lys Glu Glu Gln Ser Leu Pro Ala Gly Ala Gln Glu Ala Leu Ser
                485                 490                 495

Asp Gly Leu Gln Leu Glu Val Gln Pro Ser Glu Glu Ala Arg Gly
            500                 505                 510

Tyr Ile Val Thr Asp Arg Glu Val Leu Gly Pro Ala Val Thr Phe Lys
                515                 520                 525

Val Ser Ala Asn Val Gln Asn Val Thr Thr Glu Asp Val Glu Lys Ala
530                 535                 540

Thr Val Asp Asn Lys Asp Lys Leu Glu Glu Thr Ser Gly Leu Lys Ile
545                 550                 555                 560

Leu Gln Thr Gly Val Gly Ser Lys Ser Lys Leu Lys Phe Leu Pro Pro
                565                 570                 575

Gln Ala Glu Gln Glu Asp Ser Thr Lys Phe Ile Ala Leu Thr Leu Val
            580                 585                 590

Ser Leu Ala Cys Ile Leu Gly Val Leu Leu Ala Ser Gly Leu Ile Tyr
            595                 600                 605

Cys Leu Arg His Ser Ser Gln His Arg Leu Lys Glu Lys Leu Ser Gly
        610                 615                 620

Leu Gly Gly Asp Pro Gly Ala Asp Ala Thr Ala Ala Tyr Gln Glu Leu
625                 630                 635                 640

Cys Arg Gln Arg Met Ala Thr Arg Pro Pro Asp Arg Pro Glu Gly Pro
                645                 650                 655

His Thr Ser Arg Ile Ser Ser Val Ser Ser Gln Phe Ser Asp Gly Pro
            660                 665                 670

Ile Pro Ser Pro Ser Ala Arg Ser Ser Ala Ser Ser Trp Ser Glu Glu
        675                 680                 685

Pro Val Gln Ser Asn Met Asp Ile Ser Thr Gly His Met Ile Leu Ser
690                 695                 700

Tyr Met Glu Asp His Leu Lys Asn Lys Asn Arg Leu Glu Lys Glu Trp
705                 710                 715                 720

Glu Ala Leu Cys Ala Tyr Gln Ala Glu Pro Asn Ser Ser Phe Val Ala
                725                 730                 735

Gln Arg Glu Glu Asn Val Pro Lys Asn Arg Ser Leu Ala Val Leu Thr
            740                 745                 750

Tyr Asp His Ser Arg Val Leu Leu Lys Ala Glu Asn Ser His Ser His
        755                 760                 765

Ser Asp Tyr Ile Asn Ala Ser Pro Ile Met Asp His Asp Pro Arg Asn
770                 775                 780

Pro Ala Tyr Ile Ala Thr Gln Gly Pro Leu Pro Ala Thr Val Ala Asp
785                 790                 795                 800

Phe Trp Gln Met Val Trp Glu Ser Gly Cys Val Val Ile Val Met Leu
                805                 810                 815

Thr Pro Leu Ala Glu Asn Gly Val Arg Gln Cys Tyr His Tyr Trp Pro
            820                 825                 830
```

```
         Asp Glu Gly Ser Asn Leu Tyr His Ile Tyr Glu Val Asn Leu Val Ser
                     835                 840                 845

Glu His Ile Trp Cys Glu Asp Phe Leu Val Arg Ser Phe Tyr Leu Lys
         850                 855                 860

Asn Leu Gln Thr Asn Glu Thr Arg Thr Val Thr Gln Phe His Phe Leu
         865                 870                 875                 880

Ser Trp Tyr Asp Arg Gly Val Pro Ser Ser Arg Ser Leu Leu Asp
                     885                 890                 895

Phe Arg Arg Lys Val Asn Lys Cys Tyr Arg Gly Arg Ser Cys Pro Ile
                     900                 905                 910

Ile Val His Cys Ser Asp Gly Ala Gly Arg Ser Gly Thr Tyr Val Leu
                     915                 920                 925

Ile Asp Met Val Leu Asn Lys Met Ala Lys Gly Ala Lys Glu Ile Asp
                     930                 935                 940

Ile Ala Ala Thr Leu Glu His Leu Arg Asp Gln Arg Pro Gly Met Val
         945                 950                 955                 960

Gln Thr Lys Glu Gln Phe Glu Phe Ala Leu Thr Ala Val Ala Glu Glu
                     965                 970                 975

Val Asn Ala Ile Leu Lys Ala Leu Pro Gln
                     980                 985

(2) INFORMATION FOR SEQ ID NO:4:

(i) SEQUENCE CHARACTERISTICS:
         (A) LENGTH: 2994 base pairs
         (B) TYPE: nucleic acid
         (C) STRANDEDNESS: single
         (D) TOPOLOGY: linear (ii) MOLECULE TYPE: cDNA (vi) ORIGINAL SOURCE:
          (C) INDIVIDUAL ISOLATE: Human IL-2 Beta cDNA (longer
              version)

(xi) SEQUENCE DESCRIPTION: SEQ ID NO:4:

CAGGCGGCGG GGATGGGGCC GCCGCTCCCG CTGCTGCTGC TGCTACTGCT GCTGCTGCCG        60

CCACGCGTCC TGCCTGCCGC CCCTTCGTCC GTCCCCCGCG GCCGGCAGCT CCCGGGGCGT       120

CTGGGCTGCC TGCTCGAGGA GGGCCTCTGC GGAGCGTCCG AGGCCTGTGT GAACGATGGA       180

GTGTTTGGAA GGTGCCAGAA GGTTCCGGCA ATGGACTTTT ACCGCTACGA GGTGTCGCCC       240

GTGGCCCTGC AGCGCCTGCG CGTGGCGTTG CAGAAGCTTT CCGGCACAGG TTTCACGTGG       300

CAGGATGACT ATACTCAGTA TGTGATGGAC CAGGAACTTG CAGACCTCCC GAAAACCTAC       360

CTGAGGCGTC CTGAAGCATC CAGCCCAGCC AGGCCCTCAA ACACAGCGT TGGCAGCGAG        420

AGGAGGTACA GTCGGGAGGG CGGTGCTGCC CTGGCCAACG CCCTCCGACG CCACCTGCCC       480

TTCCTGGAGG CCCTGTCCCA GGCCCCAGCC TCAGACGTGC TCGCCAGGAC CCATACGGCG       540

CAGGACAGAC CCCCCGCTGA GGGTGATGAC GCCTTCTCCG AGAGCATCCT GACCTATGTG       600

GCCCACACGT CTGCGCTGAC CTACCCTCCC GGGCCCCGGA CCCAGCTCCA CGAGGACCTC       660

CTGCCACGGA CCCTCGGCCA GCTCCAGCCA GATGAGCTCA GCCCTAAGGT GGACAGTGGT       720

GTGGACACAG ACCATCTGAT GGCGGCCCTC AGTGCCTATG CTGCCCAGAG GCCCCCAGCT       780

CCCCCCGGGG AGGGCAGCCT GGAGCCACAG TACCTTCTGC GTGCACCCTC AAGAATGCCC       840

AGGCCTTTGC TGGCACCAGC CGCCCCCCAG AAGTGGCCTT CACCTCTGGG AGATTCCGAA       900

GACCCCTCTA GCACAGGCGA TGGAGCACGG ATTCATACCC TCCTGAAGGA CCTGCAGAGG       960
```

```
CAGCCGGCTG AGGTGAGGGG CCTGAGTGGC CTGGAGCTGG ACGGCATGGC TGAGCTGATG    1020

GCTGGCCTGA TGCAAGGCGT GGACCATGGA GTAGCTCGAG GCAGCCCTGG GAGAGCGGCC    1080

CTGGGAGAGT CTGGAGAACA GGCGGATGGC CCCAAGGCCA CCCTCCGTGG AGACAGCTTT    1140

CCAGATGACG GAGTGCAGGA CGACGATGAT AGACTTTACC AAGAGGTCCA TCGTCTGAGT    1200

GCCACACTCG GGGGCCTCCT GCAGGACCAC GGGTCTCGAC TCTTACCTGG AGCCCTCCCC    1260

TTTGCAAGGC CCCTCGACAT GGAGAGGAAG AAGTCCGAGC ACCCTGAGTC TTCCCTGTCT    1320

TCAGAAGAGG AGACTGCCGG AGTGGAGAAC GTCAAGAGCC AGACGTATTC CAAAGATCTG    1380

CTGGGGCAGC AGCCGCATTC GGAGCCCGGG GCCGCTGCGT TTGGGGAGCT CCAAAACCAG    1440

ATGCCTGGGC CCTCGAAGGA GGAGCAGAGC CTTCCAGCGG GTGCTCAGGA GGCCCTCAGC    1500

GACGGCCTGC AATTGGAGGT CCAGCCTTCC GAGGAAGAGG CGCGGGGCTA CATCGTGACA    1560

GACAGAGAGG TTCTCGGACC AGCAGTGACC TTCAAAGTGA GCGCCAATGT CCAAAACGTG    1620

ACCACTGAGG ATGTGGAGAA GGCCACAGTT GACAACAAAG ACAAACTGGA GGAAACCTCT    1680

GGACTGAAAA TTCTTCAAAC CGGAGTCGGG TCGAAAAGCA AACTCAAGTT CCTGCCTCCT    1740

CAGGCGGAGC AAGAAGACTC CACCAAGTTC ATCGCGCTCA CCCTGGTCTC CCTCGCCTGC    1800

ATCCTGGGCG TCCTCCTGGC CTCTGGCCTC ATCTACTGCC TCCGCCATAG CTCTCAGCAC    1860

AGGCTGAAGG AGAAGCTCTC GGGACTAGGG GGCGACCCAG GTGCAGATGC CACTGCCGCC    1920

TACCAGGAGC TGTGCCGCCA GCGTATGGCC ACGCGGCCAC CAGACCGACC TGAGGGCCCG    1980

CACACGTCAC GCATCAGCAG CGTCTCATCC CAGTTCAGCG ACGGGCCGAT CCCCAGCCCC    2040

TCCGCACGCA GCAGCGCCTC ATCCTGGTCC GAGGAGCCTG TGCAGTCCAA CATGGACATC    2100

TCCACCGGCC ACATGATCCT GTCCTACATG GAGGACCACC TGAAGAACAA GAACCGGCTG    2160

GAGAAGGAGT GGGAAGCGCT GTGCGCCTAC CAGGCGGAGC CCAACAGCTC GTTCGTGGCC    2220

CAGAGGGAGG AGAACGTGCC CAAGAACCGC TCCCTGGCCG TGCTGACCTA TGACCACTCC    2280

CGGGTCCTGC TGAAGGCGGA GAACAGCCAC AGCCACTCAG ACTACATCAA CGCTAGCCCC    2340

ATCATGGATC ACGACCCGAG GAACCCCGCG TACATCGCCA CCCAGGGACC GCTGCCCGCC    2400

ACCGTGGCTG ACTTTTGGCA GATGGTGTGG GAGAGCGGCT GCGTGGTGAT CGTCATGCTG    2460

ACACCCCTCG CGGAGAACGG CGTCCGGCAG TGCTACCACT ACTGGCCGGA TGAAGGCTCC    2520

AATCTCTACC ACATCTATGA GGTGAACCTG GTCTCCGAGC ACATCTGGTG TGAGGACTTC    2580

CTGGTGAGGA GCTTCTATCT GAAGAACCTG CAGACCAACG AGACGCGCAC CGTGACGCAG    2640

TTCCACTTCC TGAGTTGGTA TGACCGAGGA GTCCCTTCCT CCTCAAGGTC CCTCCTGGAC    2700

TTCCGCAGAA AAGTAAACAA GTGCTACAGG GGCCGTTCTT GTCCAATAAT TGTTCATTGC    2760

AGTGACGGTG CAGGCCGGAG CGGCACCTAC GTCCTGATCG ACATGGTTCT CAACAAGATG    2820

GCCAAAGGTG CTAAAGAGAT TGATATCGCA GCAACCCTGG AGCACTTGAG GGACCAGAGA    2880

CCCGGCATGG TCCAGACGAA GGAGCAGTTT GAGTTCGCGC TGACAGCCGT GGCTGAGGAG    2940

GTGAACGCCA TCCTCAAGGC CCTTCCCCAG TGAGCGGCAG CCTCAGGGGC CTCG          2994
```

(2) INFORMATION FOR SEQ ID NO:5:

(i) SEQUENCE CHARACTERISTICS:
        (A) LENGTH: 723 amino acids
        (B) TYPE: amino acid
        (C) STRANDEDNESS: single
        (D) TOPOLOGY: linear (ii) MOLECULE TYPE: protein (vi) ORIGINAL SOURCE:

(C) INDIVIDUAL ISOLATE: Mouse IA-2 Beta Protein (xi) SEQUENCE DESCRIPTION: SEQ ID NO:5:

```
Glu Phe Gly Thr Arg Pro Pro Pro Gly Asp Ala Lys Asp Ser Pro
1               5                   10                  15

Ser Met Asp Asp Thr Leu Leu Gln Ser Leu Leu Lys Asp Leu Pro
                20                  25                  30

Gln Asn Ser Glu Val Asp Pro Leu Gly Pro Leu Lys Glu Glu Lys Ala
         35                  40                  45

Asp Ser Val Ala Gly Ala Ile Gln Ser Asp Pro Ala Glu Gly Ser Gln
     50                  55                  60

Glu Ser His Gly Thr Gly Ala Glu Gly Gln Pro Arg Glu Gln Thr Asp
65               70                  75                  80

Ala Pro Glu Thr Met Leu Gln Asp His Arg Leu Ser Asp Asp Pro Val
                 85                  90                  95

Tyr Lys Glu Val Asn Arg Leu Ser Phe Gln Leu Gly Asp Leu Leu Lys
                100                 105                 110

Asp Tyr Gly Ser Pro Leu Leu Pro Glu Gly Pro Leu Leu Glu Lys Ser
            115                 120                 125

Ser Arg Glu Glu Met Lys Lys Leu Glu Gln Pro Glu Glu Val Leu Ser
    130                 135                 140

Ser Glu Glu Glu Thr Ala Gly Val Glu His Val Arg Ser Arg Thr Tyr
145                 150                 155                 160

Ser Lys Asp Leu Phe Glu Arg Lys Pro Asn Ser Glu Pro Gln Pro Arg
                165                 170                 175

Arg Leu Glu Asp Gln Phe Gln Asn Arg Ala Pro Glu Leu Trp Glu Asp
                180                 185                 190

Glu Glu Ser Leu Lys Leu Ala Ala Gln Gly Pro Pro Ser Gly Gly Leu
            195                 200                 205

Gln Leu Glu Val Gln Pro Ser Glu Glu Gln Gln Gly Tyr Ile Leu Thr
    210                 215                 220

Gly Asn Asn Pro Leu Ser Pro Glu Lys Gly Lys Gln Leu Met Asp Gln
225                 230                 235                 240

Val Ala His Ile Leu Arg Val Pro Ser Ser Phe Phe Ala Asp Ile Lys
                245                 250                 255

Val Leu Gly Pro Ala Val Thr Phe Lys Val Ser Ala Asn Ile Gln Asn
            260                 265                 270

Met Thr Thr Ala Asp Val Ile Lys Ala Ala Asp Asn Lys Asp Gln
            275                 280                 285

Leu Glu Lys Ala Thr Gly Leu Thr Ile Leu Gln Ser Gly Ile Arg Pro
    290                 295                 300

Lys Gly Lys His Lys Leu Leu Pro His Gln Glu Gln Glu Asp Ser
305                 310                 315                 320

Thr Lys Phe Ile Leu Leu Thr Phe Leu Ser Ile Ala Cys Ile Leu Gly
                325                 330                 335

Val Leu Leu Ala Ser Ser Leu Ala Tyr Cys Leu Arg His Asn Ser His
            340                 345                 350

Tyr Lys Leu Lys Asp Lys Leu Ser Gly Leu Gly Ala Asp Pro Ser Ala
    355                 360                 365

Asp Ala Thr Glu Ala Tyr Gln Glu Leu Cys Arg Gln Arg Met Ala Val
    370                 375                 380

Arg Pro Gln Asp Arg Ser Glu Gly Pro His Thr Ser Arg Ile Asn Ser
385                 390                 395                 400
```

```
Val Ser Ser Gln Phe Ser Asp Gly Pro Met Pro Ser Pro Ser Ala Arg
            405                 410                 415

Ser Ser Thr Ser Ser Trp Ser Glu Glu Pro Val Gln Ser Asn Met Asp
            420                 425                 430

Ile Ser Thr Gly His Met Ile Leu Ala Tyr Met Glu Asp His Leu Lys
            435                 440                 445

Asn Lys Asn Arg Leu Glu Lys Glu Trp Glu Ala Leu Cys Ala Tyr Gln
450                 455                 460

Ala Glu Pro Asn Ser Ser Leu Val Ala Gln Arg Glu Glu Asn Ala Pro
465                 470                 475                 480

Lys Asn Arg Ser Leu Ala Val Leu Thr Tyr Asp His Ser Arg Ile Leu
                485                 490                 495

Leu Lys Ser Gln Asn Ser His Gly Ser Ser Asp Tyr Ile Asn Ala Ser
            500                 505                 510

Pro Ile Met Asp His Asp Pro Arg Asn Pro Ala Tyr Ile Ala Thr Gln
            515                 520                 525

Gly Pro Leu Pro Ala Thr Val Ala Asp Phe Trp Gln Met Val Trp Glu
530                 535                 540

Ser Gly Cys Ala Val Ile Val Met Leu Thr Pro Leu Ser Glu Asn Gly
545                 550                 555                 560

Val Arg Gln Cys His His Tyr Trp Pro Asp Glu Gly Ser Asn Leu Tyr
                565                 570                 575

His Val Tyr Glu Val Asn Leu Val Ser Glu His Ile Trp Cys Gln Asp
            580                 585                 590

Phe Leu Val Arg Ser Phe Tyr Leu Lys Asn Leu Gln Thr Asn Glu Thr
            595                 600                 605

Arg Thr Val Thr Gln Phe His Phe Leu Ser Trp Tyr Asp Gln Gly Val
610                 615                 620

Pro Ser Ser Thr Arg Ser Leu Leu Asp Phe Arg Arg Lys Val Asn Lys
625                 630                 635                 640

Cys Tyr Arg Gly Arg Ser Cys Pro Ile Ile Val His Cys Ser Asp Gly
                645                 650                 655

Ala Gly Arg Ser Gly Thr Tyr Val Leu Ile Asp Met Val Leu Asn Lys
            660                 665                 670

Met Ala Lys Gly Ala Lys Glu Ile Asp Ile Ala Ala Thr Leu Glu His
            675                 680                 685

Leu Arg Asp Gln Arg Pro Gly Met Val Gln Thr Lys Glu Gln Phe Glu
690                 695                 700

Phe Ala Leu Thr Ala Val Ala Glu Glu Val Asn Ala Ile Leu Lys Ala
705                 710                 715                 720

Leu Pro Gln (2) INFORMATION FOR SEQ ID NO:6:

(i) SEQUENCE CHARACTERISTICS:
        (A) LENGTH: 2351 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (C) INDIVIDUAL ISOLATE: Mouse IA-2 Beta cDNA (xi) SEQUENCE DESCRIPTION: SEQ ID NO:6:
```

```
GAATTCGGCA CGAGGCCTCC ACCTCCTGGA GACGCCAAAG ACTCCCCGAG TATGGATGAT      60
GACACACTCC TGCAGAGTCT CCTGAAGGAT TTGCAGCAGA ACTCTGAAGT GGACCGCCTG     120
GGCCCCCTGA AGGAGGAGAA AGCAGACTCA GTTGCTGGAG CCATACAAAG TGATCCTGCA     180
GAGGGAAGCC AAGAAAGCCA CGGGAGAGGG GCTGAAGGAC AGCCAAGAGA GCAGACAGAT     240
GCCCCAGAGA CAATGCTTCA AGATCACAGA CTATCAGATG ACCCAGTGTA CAAGGAGGTC     300
AACCGTCTGA GCTTCCAGCT TGGGGACCTC TTGAAGGACT ATGGGTCTCC TCTCTTACCT     360
GAAGGTCCCC TTCTAGAAAA ATCCTCCAGA GAAGAGATGA AGAAGCTAGA GCAGCCAGAG     420
GAGGTCTTGT CTTCAGAAGA GGAGACTGCT GGGGTGGAGC ATGTGAGGAG CCGGACTTAC     480
TCCAAAGACC TATTTGAAAG GAAACCAAAC TCAGAGCCCC AGCCCAGGAG GCTTGAGGAT     540
CAGTTCCAAA ACCGAGCTCC AGAGTTGTGG GAGGATGAAG AAAGCCTCAA ATTGGCAGCA     600
CAGGGACCCC CTAGTGGAGG CCTACAGCTG GAAGTGCAGC CTTCTGAGGA ACAGCAGGGA     660
TACATCCTCA CAGGAAACAA CCCTCTAAGT CCAGAGAAGG GGAAGCAGCT GATGGACCAA     720
GTTGCCCACA TCCTCCGGGT ACCTTCCAGC TTCTTTGCAG ATATCAAAGT TTTGGGACCA     780
GCAGTGACCT TCAAAGTAAG TGCCAACATC CAAAACATGA CAACTGCCGA TGTCATCAAG     840
GCTGCAGCTG ACAACAAAGA CCAGCTGGAG AAGGCAACTG GACTGACAAT CCTTCAAAGT     900
GGAATCAGGC CGAAGGGAAA GCACAAACTC CTGCCGCATC AGGAAGAGCA AGAGGACTCT     960
ACCAAGTTCA TTTTGCTCAC CTTCCTCTCC ATTGCCTGCA TCCTGGGGGT TCTCCTGGCT    1020
TCCAGCCTTG CCTACTGCCT CCGCCACAAC TCACACTACA AGCTGAAGGA CAAGTTGTCT    1080
GGACTAGGCG CTGACCCCAG TGCAGATGCC ACTGAAGCCT ACCAGGAGCT ATGCCGCCAG    1140
CGTATGGCTG TTCGTCCACA GGACCGCTCT GAGGGACCAC ATACATCACG CATCAACAGC    1200
GTCTCATCCC AGTTCAGCGA TGGGCCGATG CCTAGTCCTT CGGCTCGGAG CAGCACTTCA    1260
TCCTGGTCTG AGGAGCCTGT CCAGTCCAAC ATGGACATCT CTACTGGCCA CATGATCCTG    1320
GCCTACATGG AAGACCATCT GAAGAACAAG AACCGCCTGG AGAAGGAGTG GGAAGCACTG    1380
TGCGCCTACC AAGCAGAGCC CAACAGCTCA CTTGTGGCCC AGAGAGAGGA GAATGCACCC    1440
AAGAACCGTT CCCTGGCTGT GCTGACCTAT GACCACTCCA GGATCCTGTT GAAGTCTCAA    1500
AACAGCCATG GCAGTTCCGA CTACATCAAT GCCAGCCCCA TTATGGACCA TGACCCACGA    1560
AACCCCGCAT ACATTGCCAC CCAAGGCCCA CTTCCCGCCA CGGTGGCCGA CTTCTGGCAG    1620
ATGGTGTGGG AAAGCGGCTG TGCAGTCATT GTCATGCTGA CACCCCTCTC CGAGAACGGC    1680
GTCCGGCAGT GCCATCACTA CTGGCCCGAT GAAGGCTCCA ACCTCTACCA TGTCTACGAG    1740
GTCAATCTAG TCTCTGAGCA CATATGGTGC CAGGATTTCC TGGTGAGAAG CTTTTACCTG    1800
AAGAACCTGC AGACCAACGA GACTCGCACG GTGACCCAGT TCCACTTCCT GAGTTGGTAT    1860
GACCAGGGAG TCCCTTCCTC CACGAGGTCA CTCCTGGATT TCCGCAGAAA AGTGAACAAA    1920
TGCTACCGAG GCCGCTCTTG TCCGATCATT GTCCATTGCA GTGACGGCGC CGGCAGGAGT    1980
GGAACCTACG TCCTGATTGA CATGGTTCTC AATAAGATGG CCAAAGGTGC TAAAGAGATT    2040
GATATCGCAG CGACCCTGGA GCACTTGAGG GACCAGAGAC CAGGCATGGT CCAGACAAAG    2100
GAGCAGTTTG AGTTTGCGCT GACAGCTGTG GCTGAGGAGG TGAATGCCAT CCTGAAGGCC    2160
CTTCCCCAGT AGGCGCTGAA GCTGGAGCTG GCGGACCCC ACCACGAGTG CTTCCAGAAC     2220
CGCAACAGGA TATCAGTCCT GCATCTTCTG TGTAGTAACA GGGTCCTTCG GGCTCCACAG    2280
TCAGTGCAGG TGGCTAGTCA TGTGTACTTC TGATTGACCA AATAGCACAT GTGTGGAAAC    2340
ACCCAGGAAG G                                                        2351
```

MATERIALS AND METHODS FOR DETECTION AND TREATMENT OF INSULIN-DEPENDENT DIABETES

This invention was made with government support under National Institutes of Health grant numbers R01 HD 19469, P01 DK39079 and GCRC M01 RR00082. The government has certain rights in the invention.

FIELD OF INVENTION

The method and compositions of this invention provide an effective and reliable substitute for the currently employed ICA assay for diabetes. By providing a method for detecting autoantibodies to IA-2β and other molecules such as the $GAD_{65}$ and IA-2 auto-antigens, the method provides a chemical assay which has improved reliability. In addition, these antigens may be employed in therapeutic regimens for the amelioration of the clinical condition.

BACKGROUND OF THE INVENTION

Diabetes is a term that refers to a collection of diseases resulting in disordered energy metabolism and varying degrees of blood glucose elevations or hyperglycemia. One of the best characterized forms of the disease is that resulting in immunologically mediated destruction of the insulin secreting pancreatic beta cells. This severe form of the disease is termed Insulin-dependent Diabetes (IDD) since it is associated with progressive insulin deficiency and coincident symptoms such as weight loss, glycosuria and polyuria, and increased thirst or polydipsia. Other terms for this form of diabetes are Type 1 Diabetes (cf. Type 2 Diabetes which results from an inherent resistance to insulin action); Ketosis Prone Diabetes because there is abnormal generation of ketone bodies as a result of excessive breakdown of body fats due to the severe insulin deficiency; or Juvenile Diabetes, since virtually all diabetes that appears in childhood and adolescence is of this type (see Atkinson and Maclaren [1994] *N. Engl. J. Med.* 331:1428–1436).

Diabetes is a major public health problem, especially in Western countries. The incidence rates vary greatly worldwide, from as high as 40 per 100,000 persons in Finland to as low as 1–2 per 100,000 among Japanese, with the US in between. The peak incidence is during the pubertal years associated with increasing bodily demands for insulin associated with muscle growth. The prevalence rates in the US population under age 20 years is 0.25% and it approaches 0.4% over a lifetime, albeit an estimated 10–20% of patients with Non Insulin-dependent Diabetes (NIDD) or Type 2 or Maturity Onset Diabetes also have, in reality, slowly progressive IDD. Thus, it is estimated that there should be at least 1 million Americans affected by IDD.

Diabetes results in progressive damage to the blood vessels of the body, to a degree that depends upon the severity of hyperglycemia and its duration. The incident mortality rate for IDD has been calculated to be 7-fold higher than for age matched non diabetic controls. Whereas the decade long Diabetes Control and Complications Trial (DCCT) concluded in 1994 by the National Institutes of Health in the US showed that meticulous insulin replacement therapy would slow the appearance of damaged arteries, it was not able to prevent this since blood glucose levels were never kept within normal limits. Ocular complications of diabetes are the leading cause of new blindness in persons of 20–74 years of age. The risk of lower extremity amputation is 15-fold higher in those with diabetes, while more than half of the approximately 125,000 persons undergoing lower limb amputation do so as a direct consequence of diabetes. Approximately 40% of persons undergoing renal transplantations have kidney failure because of their diabetes, and the proportion due to diabetes continues to rise each year. Women with diabetes produce newborn infants with a 7% newborn mortality rate, albeit this outcome can be greatly improved with tight glycemic control during the gestation period. Other complications of diabetes include increased heart disease and stroke, loss of nerve cells or neurones innervating the limbs and intestine, impotence and infertility, cataract formation in the lens of the eyes, increased periodontal disease, and predisposition to infectious diseases especially from bacteria and yeast. Of all patients with diabetes, those with IDD have a disproportionate share of these complications because of its severity and usual early age of onset. In the US, the direct health care costs attributable to diabetes in 1994 have been estimated to exceed $120 billion. Thus it is important that the pathogenesis of IDD be understood and strategies be developed to prevent it as a fully expressed clinical disease.

Patients with IDD are unusually prone to other diseases that have become recognized to have autoimmune origins. These diseases include thyroiditis or Hashimoto disease, Graves disease, Addison disease, atrophic gastritis and pernicious anemia, celiac disease and vitiligo (Maclaren, N. K. [1985] *Diabetes Care* 8(suppl.):34–38). Evidence that IDD itself has an autoimmune nature began with histological studies of patients that succumbed at diagnosis which indicated that the islets were infiltrated with a chronic inflammatory (lymphocytic) infiltrate termed insulitis. This was supported in the early 1970s by reports of islet cell autoantibodies reactive to antigens within the cytoplasm (ICA) (Lendrum et al. [1975] *Lancet* 1:880–882) or confined to the islet cell surfaces (ICSA) (Maclaren et al. [1975] *Lancet* 1:977–1000) as detectable by indirect immunofluorescence. Later it was recognized that many patients also develop autoantibodies to insulin (IAA) before their diagnosis (Palmer et al. [1983] *Science* 222:1337–1339) as well as to insulin receptors (Maron et al. [1983] *Nature* 303:817–818). Autoantibodies were also reported to an islet cell protein composition of 64,000 M.Wt. in man (Baekkeskov et al. [1982] *Nature* 298:167–169), in the Biobreeding (BB) rat model (Baekkeskov et al.[1984] *Science* 224:1348–1350) and in the Non Obese Diabetic (NOD) mouse model (Atkinson and Maclaren [1988] *Diabetes* 37:1587–1590). 64 kDa antigen has subsequently been reported to be the lower molecular weight isoform of glutaric acid decarboxylase ($GAD_{65}$) (Baekkeskov et al. [1990] *Nature* 347:151–156) (Kauffman et al. [1992] *J. Clin. Invest.* 283–292). GAD is an enzyme that converts glutamate into the membrane stabilizing neurotransmitter called gamma amino butyric acid or GABA. In addition to autoantibodies to GAD, peripheral blood mononuclear cells were shown to be autoreactive in patients developing IDD (Atkinson and Maclaren et al. [1992] *Lancet* 339:458–459; and Harrison et al. [1993] *Lancet* 341:1365–1369). Indeed a leading possible cause for IDD is that immunity to enteroviral proteins (developed through infection by Coxsackie or closely related viruses) that have structural homologies to GAD, may in the genetically predisposed individual, trigger an autoimmune response to islet cells because of this molecular mimicry (Atkinson and Maclaren [1990] *Scientific American* 262:61–71; Kauffnman et al. [1992] *J. Clin. Invest.* 89:283–292; Atkinson, Maclaren et al. [1994] *J. Clin. Invest.* 94:2125–2129).

Since immunological markers predate the clinical onset of IDD often by many years, their possible value in disease prediction became increasingly realized (Maclaren, N. K. [1988] *Diabetes* 37:1591–1594), permitting in turn options for therapeutically induced delays in diabetes onset to be considered (Muir and Maclaren [1993] *J. Autoimmunity* 16:301–310). Indeed by 1994, multicenter trials attempting to prevent IDD through prophylactic parenteral insulin or oral insulin therapies had been initiated in the US (the DPT-1 trial), as well as in Europe using prophylactic nicotinamide (the ENDIT trial). Among relatives, the appearance of IAA was shown to predate onset of IDD (Atkinson and Maclaren [1985] *Diabetes* 35:894–898) while ICA proved to be valuable to the prediction of IDD in relatives (Riley, Maclaren et al. [1990] *N. Engl. J. Med.* 323:1167–1172) as well as in the general population (Schatz, Maclaren et al. [1994] *J. Clin. Invest.* 93:2403–2407), as modifiable on the basis of coincident IAA (Krischer, Maclaren et al. [1993] *J. Clin. Endo. Metab.* 77:743–749). While not ideal, the predictability of IDD based upon the ICA test provided the basis for the DPT-1 and ENDIT trials mentioned above. Furthermore, autoantibodies to the 64 kDa islet cell protein also proved to have utility in IDD prediction (Atkinson, Maclaren et al. [1990] *Lancet* 335:1357–1360), as eventually realized by the chemical assay for autoantibodies to $GAD_{65}$ (Schott, Maclaren et al. [1994] *J. Autoimmunity* 7:865–872). These studies made it important to resolve the nature of all of the islet cell autoantigens involved in the pathogenesis of IDD (Atkinson and Maclaren [1993] *J. Clin. Invest.* 92:1608–1616). Whereas ICA, as determined by indirect immunofluorescence of human cryocut pancreatic sections, was likely to represent multiple autoantigens (Genovese et al. [1992] *Diabetologia* 35:385–388), GAD soon proved to be one of these (Atkinson, Maclaren et al. [1993] *J. Clin. Invest.* 91:350–356). Insulin, however, was not a component of ICA unless the pancreatic sections were first chemically "fixed" before being used as tissue substrate.

Recently, a 3.6-kb cDNA with a 2,937-bp open reading frame was isolated from a human insulinoma subtraction library (ISL-153) as described by Lan et al. ([1994] *DNA and Cell Biology* 13:505–514, herein incorporated by reference). The predicted amino acid sequence and in-vitro-translated product of IA-2 cDNA revealed a 979-amino acid protein with a PI value of 7.09 and a molecular mass of 105,847 daltons. The protein sequence is consistent with a signal peptide, an extracellular domain, a transmembrane domain and an intracellular domain. The extracellular domain contains an unusual cysteine-rich region following the signal peptide. The intracellular cytoplasmic domain of IA-2 possesses highly conserved regions similar to the catalytic domains in members of the protein tyrosine phosphatase (PTP) family. Northern blot analyses showed that IA-2 mRNA was expressed in five of five freshly isolated human insulinomas, rat and mouse insulinoma cell lines, and in enriched normal mouse islets. It was also found in normal human brain, pituitary, pancreas, and brain tumor cell lines, but not in a variety of other normal or tumor tissues. Based on the sequence and expression data, it appears that IA-2 is a new member of the receptor-type PTP family that is expressed in islet and brain tissues. The involvement of the molecule in beta cell autoimmunity or IDD was queried but was not disclosed or suggested in that work.

More recently, Payton et al. ([1995] *J. Clin. Invest.* 96:1506–1511) reported on the relationship of 37 kDa and 40 kDa tryptic fragments of islet antigens in IDD to the IA-2 molecule reported by Lan et al., supra. Payton et al. concluded that the 40 kDa fragment is a tryptic product of the IA-2 molecule but that the 37 kDa molecule, while sharing some antigenic determinants with the 40 kDa molecule, was a fragment of an as yet unidentified molecule.

We report herein, for the first time, the amino acid sequence and nucleotide sequence of both the mouse and the human counterparts of a new IDD associated autoantigen, referred to herein as IA-2β. This antigen, alone or in combination with other IDD associated antigens such as IA-2 and $GAD_{65}$, is useful in the prediction (diagnosis), treatment (therapy), and prevention (prophylaxis) of diabetes.

BRIEF SUMMARY OF THE INVENTION

The invention described herein concerns a novel means of accurately detecting the early stages of IDD, such that risk for the disease can be assessed. Also described are means of treating IDD and thereby preventing the occurrence of its clinical manifestations.

It has been found that autoantibodies to islet cells (ICA) can be used as important predictors of IDD. However, their predictive value in individuals found to have them is quite variable. When found in the absence of IAA, they give an overall predictability for IDD of about 1 in 4 over 5 years, but the rate of progression to IDD rises up to 2 in 3 when found together with IAA, at least in non-diabetic relatives of patients with IDD (Krischer, Maclaren et al. [1994] *J. Clin. Endo. Metab.* 77:743–749). Among non diabetic relatives of families affected by IDD who are under the age of 10 years when ICA are discovered, ICA strongly predicts IDD (Riley, Maclaren et al. [1990] *N. Engl. J. Med.* 323:1167–1172). The instant invention is based on the component autoantibodies and autoantigens that comprise the ICA reaction, which provide differential information as to the degree of predictive power of ICA Appearance of these component autoantibodies aids in the identification of the stage of the disease and thus in the time to clinical diagnosis. The indirect immunofluorescence based ICA test is cumbersome to perform, and does not replicate as well as chemically based assays. One component of the ICA reaction is that explained by autoantibodies to $GAD_{65}$, and this latter determination has become available through immunoassays.

A second autoantibody component of the ICA reaction, which is directed to an islet cell member of the receptor type of the tyrosine phosphatase family, is termed IA-2. The human IA-2 gene product has been identified as a major autoantigen of importance to IDD. We sequenced and cloned the IA2 gene, and expressed the gene product in rabbit reticulocytes, to detect the corresponding autoantibody. Detection of autoantibodies to the $GAD_{65}$ and to IA-2 antigens effectively substitutes for the cumbersome and less than completely reliable ICA assay with a reliable, chemically based assay. Further, the availability of recombinant IA-2 permits the antigen to be used alone or in combination with other antigens in a therapeutic regimen to delay the onset or progression of clinical IDD.

According to the instant disclosure, we disclose a third major component of the ICA reaction. A novel molecule, referred to herein as IA-2β, may be used alone or in combination with $GAD_{65}$ and IA-2 to increase and broaden the predictive power of an assay based on IDD associated antigens. The nucleotide and amino acid sequences of this new autoantigen are disclosed, as are diagnostic, prophylactic and therapeutic uses thereof.

A further embodiment of the subject invention concerns the use of fragments of the full-length IA-2 and/or IA-2β molecules to detect antibodies to IA-2 and IA-2β. Such fragments of IA-2 would, preferably, be larger than the fragment known as ICA 512 as described by Rabin et al. (Rabin et al. [1994] *Journal of Immunology* 152:3183–3188)

and larger than 37 kDa to about 40 kDa fragments obtainable by trypsin degradation of the full-length proteins.

Accordingly, it is an object of this invention to provide methods and compositions for the immune detection of insulin-dependent diabetes and susceptibility to IDD.

Another object of the invention is to provide methods and compositions for the immunoprophylaxis and treatment of IDD. Other objects of the invention will become clear from the complete disclosure.

BRIEF DESCRIPTION OF THE DRAWINGS

FIG. 1. Amino acid sequences of mouse IA-2β and IA-2. Protein sequences were lined up with a GCG BESTFIT program. Identical amino acid residues are shown by (|), highly similar amino acids by (:), and similar amino acids by (.). The putative transmembrane segment (TM) is shown in an open box and the PTP core sequence in a shaded box. Residue numbers represent mouse IA-2 (Lu, J., A. L. Notkins, M. S. Lan [1994] *Biochem. Biophys. Res. Commun.* 204:930–936). The amino acid terminal of the partial mouse IA-2β protein sequence was arbitrarily designated residue number one. Arrows indicate the start of the intracellular sequences constructed in the pCRII vector for the in vitro translation study.

FIG. 4A: Radiolabeled recombinant intracellular domain of IA-2 and IA-2β were immunoprecipitated by two different hyperimmune rabbit antisera or a mouse monoclonal antibody raised against the PTP domain of the IA-2 molecule. FIG. 4B: In vitro radiolabeled intracellular domains of IA-2 and IA-2β were precipitated with sera from IDD patients. Sera were pre-incubated with PBS or unlabeled (*) in vitro translated recombinant IA-2 or IA-2β (10-fold excess as compared to radiolabeled antigen) for 2 hours, then the radiolabeled antigen was added. IA-2R and IA-2βR are the respective anti-sense in vitro translation products. "H" represents higher concentration (50-fold excess as compared to radiolabeled antigen) of in vitro translated recombinant IA-2 or IA-2β for blocking.

Brief Description of the Sequences

Figures 2A, 2B:
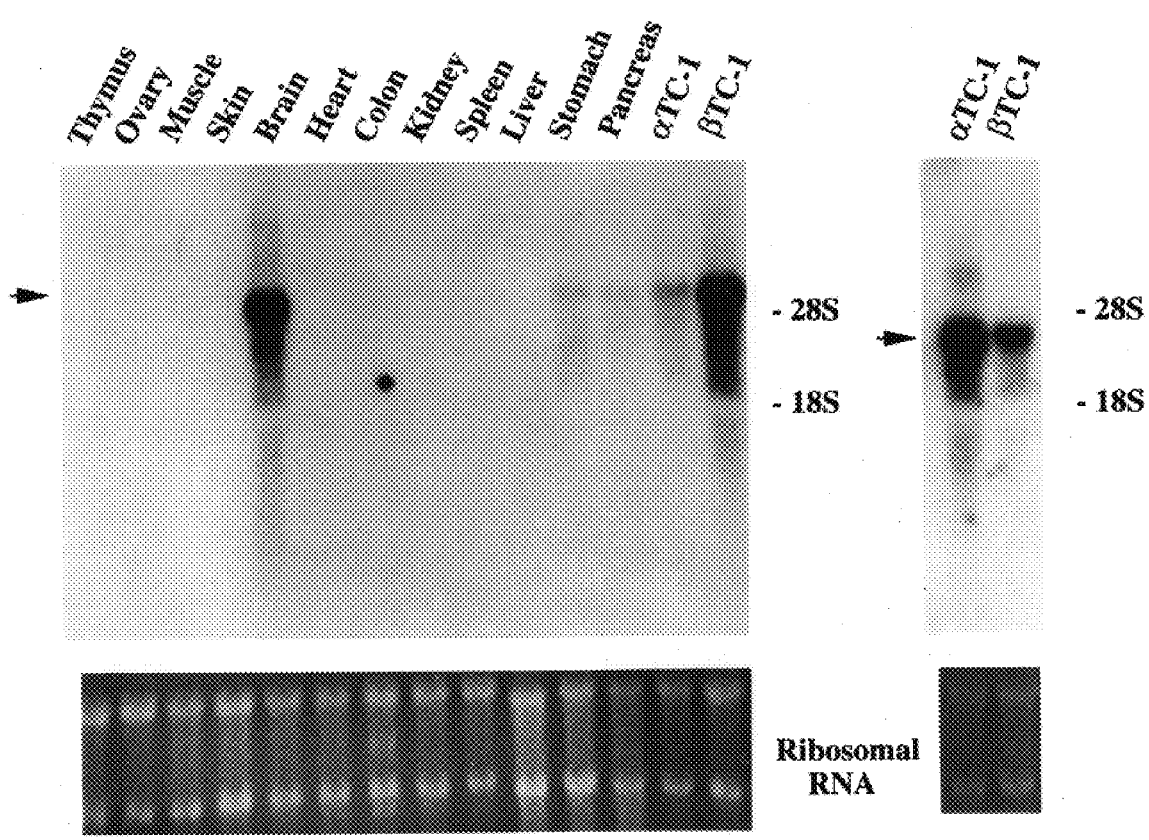
FIGS. 2A–2B. Northern analysis. Total RNA (20 μg) from normal mouse tissues and cell lines were separated on a 1% agarose/formaldehyde gel, transferred to a Nytran membrane and hybridized with $^{32}$P-labeled IA-2β cDNA probe (2A) or IA-2 cDNA probe (2B). Message sizes of IA-2, 3.8 kb (arrow), and IA-2β, 5.5 kb (arrow), were estimated by ribosomal RNAs. Ribosomal RNAs are shown at the bottom of the blot.

SEQ ID NO. 1 is the amino acid sequence of human IA-2β protein (shorter version).

SEQ ID NO. 2 is the nucleotide sequence of full length human IA-2β cDNA (shorter version).

SEQ ID NO. 3 is the amino acid sequence of human IA-2β protein (longer version).

SEQ ID NO. 4 is the nucleotide sequence of full length human IA-2β cDNA (longer version).

SEQ ID NO. 5 is the amino acid sequence of mouse IA-2β protein.

SEQ ID NO. 6 is the nucleotide sequence of mouse IA-2β cDNA.

DETAILED DESCRIPTION OF THE INVENTION

The invention described here relates to the detection of antibodies to insulinoma-associated antigen-2 (IA-2), and insulinoma-associated antigen-2β (IA-2β) alone or in combination with other antigens, as an accurate and specific early indicator of the onset of Insulin-dependent Diabetes (IDD).

IA-2 has been recently identified as a member of the transmembrane protein tyrosine phosphatase family. The complete amino acid sequence of IA-2 has been determined and the protein can be expressed as described herein in bacteria or eukaryotic cells.

Of sera from 55 diabetic patients, 45.4% reacted by ELISA with IA-2 expressed as intracellular and extracellular components in *E. coli* as compared to only 7.5% of normal controls. Analysis of newly-diagnosed (less than one year) IDD patients revealed that 50% reacted with IA-2 as did 38% of patients with longer term diabetes. Reactivity of IDD sera with glutamic acid decarboxylase (GAD$_{65}$) as compared to reactivity with IA-2 showed that 60% of GAD$_{65}$-negative IDD sera were positive for IA-2. Further experiments revealed that both rabbit antibody raised to IA-2, and human IDD sera positive for IA-2 antibody and affinity purified by passage through an IA-2 column, specifically stained cells in the pancreatic islets of Langerhans, but not surrounding acinar tissue.

We present herein a novel cDNA, IA-M, isolated from a mouse neonatal brain library and a human counterpart thereof cloned using the mouse cDNA. Our data indicates that IA-2β is a major autoantigen in IDD. We have developed a very sensitive radioimmune-precipitation assay to test for autoantibodies to the intracellular domain of IA-2β in sera of patients with IDD and individuals who are at high risk of developing IDD. Our data show that 46% of sera from IDD patients react with the intracellular domain of IA-2β whereas none of the sera from normal controls react with IA-2β. The intracellular domain of mouse IA-2β yields considerable information. An even higher percentage of IDD sera scored positive when the entire sequence of IA-2β is used, particularly when the human protein is substituted as the ligand. IA-2β is also useful as a therapeutic reagent in preventing diabetes. Both the diagnostic and therapeutic values of IA-2β autoantigen will have a profound impact on the treatment of the diabetes.

One aspect of the subject invention is the discovery of IA-2β and that it is an autoantigen in IDD and is responsible for some of the staining of islets by islet-cell autoantibody positive sera, especially those negative for reactivity to the $GAD_{65}$ antigen and the IA-2 antigen. These findings indicate that testing for autoantibodies to $GAD_{65}$, IA-2, and IA-2β can be used to provide a reliable method for identifying IDD patients using chemical assays which are more reproducible than possible using the indirect immunofluorescence for ICA.

IA-2 is a 105,847 kDa transmembrane protein that belongs to the protein tyrosine phosphatase family. Immunoperoxidase staining with antibody raised against IA-2 confirms that this protein is expressed in human pancreatic islet cells. The subject invention, the full-length cDNA clone of IA-2 can be expressed in a rabbit reticulocyte transcription/translation system and the recombinant radio-labelled IA-2 used as an antigen to detect autoantibodies by immunoprecipitation. IA-2β can be used in a similar fashion.

IA-2 and IA-2β can be expressed, isolated and used as antigens to produce immune tolerance and/or immunosuppression to ameliorate or prevent IDD. IA-2 or IA-2β may also be introduced into a patient with an adjuvant, such as alum, or as diphtheria pertussis and tetanus (DPT) or any other adjuvant accepted for introduction into people such as to create an immunization to the antigen. Furthermore, these antigens can be expressed in a recombinant viral vaccine or the DNA coding for IA-2 or IA-2β or both could be introduced into an individual for expression in muscle or other cells to achieve immune tolerance and thus prevent or ameliorate IDD. Further, the antigen or fragments thereof can be given intravenously to down regulate autoimmune islet responses and thereby to prevent or treat IDD.

One hundred coded sera were tested by this method, 50 from patients with newly diagnosed IDD and 50 from age-matched normal controls. Sixty-six percent of the sera from patients, but none of the sera from controls, reacted with IA-2. The same diabetic sera tested for autoantibodies to glutamic acid decarboxylase ($GAD_{65}Ab$) by depletion-ELISA (d-ELISA) and to islet cells by indirect immunofluorescence showed 52% and 68% positivity, respectively. Up to 86% of the IDD patients had autoantibodies to IA-2 and/or $GAD_{65}$. Patients diagnosed with IDD before age 20 were more likely to have autoantibodies to IA-2 than patients diagnosed after age 20. Over 90% (14 of 15) of sera that were ICA-positive, but $GAD_{65}$ Ab-negative, had autoantibodies to IA-2. Absorption experiments showed that the immunofluorescence reactivity of sera containing ICA was greatly reduced by prior incubation with recombinant IA-2 or $GAD_{65}$ when the respective antibody was present. Thus IA-2 is a major islet cell autoantigen in IDD pathogenesis, and is responsible, in part, for the reactivity of ICA with pancreatic islets. Tests for the detection of autoantibodies to recombinant IA-2 and $GAD_{65}$ have advantages over ICA as a predictor and identifier of patients with IDD.

Full-length IA-2 cDNA expressed in an eukaryotic expression system, can be used to create a radioimmunoassay for detecting autoantibodies to IA-2. Two thirds of our IDD patients had autoantbiodies to IA-2, as compared to none of the controls. The radioimmunoassay is considerably more sensitive and specific than an ELISA test which employs the full-length of the intracellular domain of IA-2. Moreover, the radioimmunoassay used here is a liquid-phase assay and is therefore more likely to detect conformational epitopes than solid-phase ELISA Fragments of the full-length protein can also be used.

We have isolated a novel cDNA, IA-2β from a mouse neonatal brain library. The predicted protein sequence revealed an extracellular domain, a transmembrane region and an intracellular domain. Northern analysis showed that the message size of IA-2β is approximately 5.5 kb. Its intracellular domain is 376 amino acids long and 76% identical to the intracellular domain of IA-2, a major autoantigen in IDD. A partial sequence of the extracellular domain of IA-2β indicates that it differs substantially (only 26% identical) from that of IA-2. Both molecules are expressed in islets and brain tissue, but based on analysis of islet cell tumor lines, IA-2β appears to be expressed predominantly in β cells, and IA-2 in α cells. The recombinant intracellular domain of IA-2β was tested for reactivity with sera from IDD patients by immunoprecipitation. Forty-six percent (23/50) of diabetic sera, but none of the sera from normal control (0/50) reacted with IA-2β. Competitive inhibition experiments showed that diabetic sera have autoantibodies that recognize both common and distinct determinants on IA-2 and IA-2β.

Many IDD sera are known to immunoprecipitate 37 kDa and 40 kDa tryptic fragments from insulinoma and islet cells. The identity of the precursor protein(s) from which these fragments are derived has remained elusive. The current disclosure shows that treatment of recombinant IA-2β and IA-2 with trypsin yields 37 kDa and 40 kDa fragments of these molecules, respectively, and that these fragments are immunoprecipitated with diabetic sera. Absorption of diabetic sera with unlabeled recombinant IA-2 or IA-2β, prior to incubation with radiolabeled tryptic fragments from insulinoma or glucagonoma cells, blocks the immunoprecipitation of both the radiolabeled 37 kDa and 40 kDa tryptic fragments. We conclude that IA-2β and IA-2 are the precursors of the 37 kDa and 40 kDa islet cell autoantigens, respectively, and that both IA2 and IA-2β are major autoantigens in IDD.

Accordingly, it is noted that IA-2 is a novel receptor-type PTP isolated from a human insulinoma subtraction library (Lan, M. S., J. Lu, Y. Goto, A. L. Notkins [1994] *DNA and Cell Biology* 13:505–514) and is now known to be a major autoantigen in IDD. We identified 21 PTPs in pancreatic islets, three of which were novel. In the present disclosure, the entire sequence of the murine intracellular and transmembrane domain and a partial sequence of the extracellular domain of one of these novel PTPs, IA-2β is revealed. The complete human sequences are disclosed herein. Our data indicates that IA-M is closely related, but different from IA-2. The intracellular domain of IA-2β shows 74% identity to the intracellular domain of IA-2. The PTP core sequence differs by only one amino acid. A partial sequence (322 amino acids) of the extracellular domain of IA-2β, however, shows only 26% identity to the extracellular domain of IA-2.

As disclosed herein the tissue distribution of IA-2β and IA-2 shows similarities, but also some differences. IA-2β and IA-2 are expressed primarily in pancreatic islets and brain. Of particular interest is the fact that IA-2β is preferentially expressed in our β cell line (βTC-1), whereas IA-2 is preferentially expressed in our α cell line (αTC-1). Accordingly, this disclosure predicts that those proteins may be used differentially in disease diagnosis and treatment, based on whether or not α or β cells are the primary sites for the disease.

The intracellular domain of IA-2β, expressed in a reticulocyte transcription/translation system, was used as antigen to search for autoantibodies in the sera of diabetic patients. Our studies showed that close to 50% of sera from diabetic patients reacted with IA-2β. It is clear that many sera that react with IA-2β also react with IA-2 because of common antigenic determinants. However, screening indicates that there are unique epitopes on both IA-2 and IA-2β and that certain diabetic sera preferentially recognize one or the other of these autoantigens. Examination of a large number of diabetic sera reveals the clinical importance of these unique epitopes. The intracellular domain of mouse IA-2β has yielded considerable information. Even more data is obtained when the entire sequence of IA-2β is used, particularly when the human sequence disclosed herein is used. Human IA-2β was isolated, as disclosed herein, using mouse IA-2β cDNA as the probe.

Autoantibodies to islet cell antigens have been the subject of a number of reports (Baekkeskov, S., J. H. Nielsen, B. Marner, T. Bilde, J. Ludvigsson, A Lernmark [1982] Nature 298:167–169; Castano, L., E. Russo, L. Zhou, M. A, Lipes, G. S. Eisenbarth [1991] J. Clin. Endocrinol. & Metab. 73:1197–1201; Pietropaolo, M., L. Castano, S. Babu, R. Buelow, Y. L. Kuo, S. Martin, A. Martin, A. C. Powers, M. Prochazka, J. Naggert, E. H. Leiter, G. S. Eisenbarth [1993] J. Clin. Invest. 92:359–371; Palmer, J. P., C. M. Asplin, P. Clemons, K. Lyen, O. Tatpati, P. K. Raghu, T. L. Paquette [1983] Science 222:1337–1339; Rabin, D. U., S. M. Pleasic, J. A. Shapiro, H. Yoo-Warren, J. Oles, J. M. Hicks, D. E. Goldstein, P. M. M. Bae [1994] J. Immunol. 152: 3183–3188). In 1990, Christie et al. (Christie, M. R., G. Vohra, P. Champagne, D. Daneman, T. L Delovitch [1990] J. Exp. Med. 172:789–794) reported that a radiolabeled lysate of insulinoma cells, incubated with diabetic sera and then treated with trypsin resulted in the precipitation of 37 kDa and 40 kDa fragments. Autoantibodies to these fragments were found in a high percentage of diabetic patients and their presence in non-diabetic subjects was highly predictive of the subsequent development of IDD (Christie, M. R., R. Y. Tun, S. S. Lo, D. Cassidy, T. J. Brown, J. Hollands, M. Shattock, G. F. Bottazzo, R. D. Leslie [1992] Diabetes 41:782–787; Christie, M. R., S. Genovese, D. Cassidy, E. Bosi T. J. Brown, M. Lai E. Bonifacio, G. F. Bottazzo [1994] Diabetes 43:1254–1259; Ongagna, J. C., C. Levy-Marchal [1995] Diabetologia 38:370–375). Since autoantibodies to the 37 kDa and 40 kDa tryptic fragments showed a strong positive correlation, it was suggested that these antibodies bound to epitopes common to both fragments (Christie, M. R., J. A. Hollands, T. J. Brown, B. K. Michelsen, T. L. Delovitch [1993] J. Clin. Invest. 92:240–248). However, the identity of the precursor protein (s) from which these tryptic fragments were derived remained unclear. Recently, Christie reported, based on blocking experiments with the intracellular domain of IA-2, that IA-2 appears to be the precursor of the 40 kDa, but not the 37 kDa fragment (Payton, M. A, C. J. Hawkes, M. R. Christie [1995] J. Clin. Invest. 96:1506–1511). Our data shows that recombinant IA-2 and IA-2β yield tryptic fragments of 40 kDa and 37 kDa, respectively. Moreover, both unlabeled recombinant IA-2 and IA-2β block the binding of diabetic sera to the 40 kDa and 37 kDa tryptic fragments prepared from insulinoma cells. Therefore, we conclude that IA-2 is the precursor of the 40 kDa and IA-2β is the precursor of 37 kDa tryptic fragment, respectively.

The cloning and sequencing of IA-2 and IA-2β as well as the identification of these molecules as major autoantigens, are critical steps in elucidating their role in the pathogenesis of IDD. The development of a panel of autoantibody assays using recombinant IA-2 and/or IA-2β together with recombinant $GAD_{65}$ provides a powerful tool for screening large populations and accessing their relative predictive values in identifying individuals at high risk for IDD.

According to the disclosure provided herein, it is clear that one of ordinary skill could use either the murine or human sequences of IA-2 or IA-2β to clone the IA-2 or IA-2β sequences of other mammalian species. The IA-2 or IA-2β from these other sources could then be used in the therapeutic and diagnostic procedures of the subject invention. In addition, as those of ordinary skill in the art will appreciate, any of a number of different nucleotide sequences can be used, based on the degeneracy of the genetic code, to produce the IA-2β protein. Accordingly, any nucleotide sequence which encodes full-length mammalian IA-2β comes within the scope of this invention and the claims appended hereto. Also, as described herein, fragments of IA-2 and IA-2β are an aspect of the subject invention so long as such fragments retain the immunological activity so that such fragments are useful in therapeutic and diagnostic procedures as described herein. Such fragments can easily and routinely be produced by techniques well known in the art, for example, by time-controlled Bal31 exonuclease digestion of the full-length DNA, followed by expression of the resulting fragments and routine screening of the expression products for the desired activity.

The term "nucleic acid" refers to a deoxyribonucleotide or ribonucleotide polymer in either single- or double-stranded form, and unless otherwise limited, would encompass known analogs of natural nucleotides that can function in a similar manner as naturally-occurring nucleotides.

The phrase "nucleic acid encoding" or "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both full-length nucleic acid sequences as well as shorter sequences derived from the full-length sequences. It is understood that a particular nucleic acid sequence includes the degenerate codons of the native sequence or sequences which may be introduced to provide codon preference in a specific host cell. The nucleic acid includes both the sense and antisense strands as either individual strands or in the duplex. The terms "hybridize" or "hybridizing" refer to the binding of two single-stranded nucleic acids via complementary base pairing.

The phrase "hybridizing specifically to" refers to binding, duplexing, or hybridizing of a molecule only to a particular nucleotide sequence under stringent conditions when that sequence is present in a preparation of total cellular DNA or RNA.

The term "stringent conditions" refers to conditions under which a probe will hybridize to its target sub-sequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a complementary probe. Typically, stringent conditions will be those in which the salt concentration is at least about 0.1 to 1.0 N Na ion concentration at pH 7.0 to 7.5 and the temperature is at least about 60° C. for long sequences (e.g., greater than about 50 nucleotides) and at least about 42° C. for shorter sequences (e.g., about 10 to 50 nucleotides).

The terms "isolated" or "substantially pure" when referring to nucleic acid sequences encoding IA-2 or IA-2β proteins or fragments thereof refers to isolated nucleic acids which do not encode proteins or peptides other than IA-2 or IA-2β proteins or peptides.

The terms "isolated" or "substantially purified" when referring to IA-2 or IA-2β proteins, means a chemical composition which is essentially free of other cellular components. It is preferably in a homogenous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. Generally, a substantially purified or isolated protein will comprise more than 80% of all macromolecular species present in the preparation. Preferably, the protein is purified to represent greater than 90% of all macromolecular species present. More preferably, the protein is purified to greater than 95%, and most preferably the protein is purified to essential homogeneity, wherein other macromolecular species are not detected by conventional techniques.

The phrase "specifically binds to an antibody" or "specifically immunoreactive with," when referring to a protein or peptide, refers to a binding reaction which is determinative of the presence of the protein in a heterogeneous population of proteins and other biologics. Thus, under designated immunoassay conditions, the specified antibodies bound to a particular protein do not bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays are routinely used to select antibodies specifically immunoreactive with a protein. See Harlow and Lan (1988) *Antibodies, A Laboratory Manual,* Cold Spring Harbor Publications, New York, for a description of immunoassay formats and -conditions that could be used to determine specific immunoreactivity. The subject invention further concerns antibodies raised against the purified IA-2 or IA-2β molecules or their fragments.

The term "biological sample" as used herein refers to any sample obtained from a living organism or from an organism that has died. Examples of biological samples include body fluids, tissue specimens, and tissue cultures lines taken from patients.

The term "recombinant DNA" or "recombinantly-produced DNA" refers to DNA which has been isolated from its native or endogenous source and modified either chemically or enzymatically to delete naturally-occurring flanking nucleotides or provide flanking nucleotides that do not naturally occur. Flanking nucleotides are those nucleotides which are either upstream or downstream from the described sequence or sub-sequence of nucleotides.

The term "recombinant protein" or "recombinantly-produced protein" refers to a peptide or protein produced using non-native cells that do not have an endogenous copy of DNA able to express the protein. The cells produce the protein because they have been genetically altered by the introduction of the appropriate nucleic acid sequence. The recombinant protein will not be found in association with proteins and other subcellular components normally associated with the cells producing the protein.

The following terms are used to describe the sequence relationships between two or more nucleic acids or polynucleotides: "reference sequence," "comparison window," "sequence identity," and "percentage of sequence identity."

A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence.

"Percentage of sequence identity" is determined by comparing two optimally aligned sequences or sub-sequences over a comparison window or span, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical subunit (e.g., nucleic acid base or amino acid residue) occurs in both sequences to yield the number of matched positions, dividing the number of matched positions by the total number of positions in the window of comparison, and multiplying the result by 100 to yield the percentage of sequence identity. Percentage sequence identity when calculated using the programs GAP or BESTFIT is calculated using default gap weights. In a preferred embodiment, IA-2β sequences of the subject invention will have at least about 80% sequence identity with SEQ ID NO. 3 or SEQ ID NO. 4.

When percentage of sequence identity is used in reference to proteins or peptides, it is recognized that residue positions which are not identical may differ by conservative amino acid substitutions where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of this substitution. Means for making this adjustment are well known to those of ordinary skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of 0, a conservative substitution is given a score between 0 and 1. The scoring of conservative substitutions is calculated according to the algorithm of Meyers and Milleer (1988) *Computer Applic. Biol. Sci.* 4:11–17 as implemented in the program PC/GENE (Intelligenetics, Mountain View, Calif., USA). The following six groups each contain amino acids that are conservative substitutions for one another:

1. Alanine (A), Serine (S), Threonine (T);
2. Aspartic acid (D), Glutamic acid (E);
3. Asparagine (N), Glutamine (Q);
4. Arginine (R), Lysine (K);
5. Isoleucine (I), Leucine (L), Methionine (M), Valine (V); and
6. Phenylalanine (F), Tyrosine (Y), Tryptophan (W).

A "comparison window," as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Methods of alignment of sequences for comparison are well known in the art. Optimal alignment of sequences for comparison may be conducted by the local homology algorithm of Smith and Waterman (1981) *Adv. Appl. Math.* 2:482, which is incorporated herein by reference; by the homology alignment algorithm of Needleman and Wunsch (1970) *J. Mol Biol.* 48:443, which is incorporated herein by reference; by the search for similarity method of Pearson and Lipman (1988) *Proc. Natl. Acad. Sci. USA* 85:2444, which is incorporated herein by reference; by computerized implementations of the algorithms (including, but not limited to, CLUSTAL in the PC/GENE program by Intelligenetics, GAP, BESTFIT, PASTA, and TFASTA in Wisconsin Genetics Software Package, Genetics Computer Group (GCG), 575 Science Drive, Madison, Wis., USA) or by inspection. In particular, methods for aligning sequences using the CLUSTAL program are well described by Higgins and Sharp (1988) *Gene* 73:237–244 and (1989) CABIOS 5:151–153, both of which are incorporated herein by reference.

Expression of IA-2 or IA-2β proteins. Once DNA encoding IA-2 or IA-2β proteins is isolated and cloned, one can express the IA-2β proteins in a variety of recombinantly engineered cells. It is expected that those of ordinary skill in the art are knowledgeable in the numerous expression systems available for expression of DNA encoding IA-2 or IA-2β proteins.

In brief summary, the expression of natural or synthetic nucleic acids encoding proteins will typically be achieved by operably liking the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of polynucleotide sequences encoding IA-2 or IA-2β proteins. To obtain high level expression of a cloned gene such as those polynucleotide sequences encoding IA-2 or IA-2β proteins, it is desirable to construct expression plasmids which contain at the minimum a strong promoter to direct transcription, a ribosome binding site for translational initiation, and a transcription/translation terminator. The expression vectors may also comprise generic expression cassettes containing at least one independent terminator sequence, sequences permitting replication of the plasmid in both eukaryotes and prokaryotes, i.e., shuttle vectors, and selection markers for both prokaryotic and eukaryotic systems. See Maniatis, T., E. F. Fritsch, J. Sambrook (1989) *Molecular Cloning: A Laboratory Manual,* 2d Edition, Cold Spring Harbor Laboratory, Cold Spring Harbor, N.Y.

Expression in prokaryotes. A variety of prokaryotic expression systems may be used to express IA-2 or IA-2β proteins. Examples include *E. coli,* Bacillus, Streptomyces, and the like. For example, IA-2 or IA-2β proteins may be expressed in *E. coli.*

It is essential to construct expression plasmids which contain, at the minimum, a strong promoter to direct transcription, a ribosome binding site for translational initiation, and a transcription/translation terminator. Examples of regulatory regions suitable for this purpose in *E. coli* are the promoter and operator region of the *E. coli* tryptophan biosynthetic pathway as described by Yanofsky (1984) *J. Bacteriol.* 158:1018–1024 and the leftward promoter of phage lambda (Pλ) as described by Herskowiitz et al. (1980) *Ann. Rev. Genet.* 14:399–445. The inclusion of selection markers in DNA vectors transformed in *E. coli* is also useful. Examples of such selection markers include genes specifying resistance to ampicillin, tetracycline, or chloramphenicol. See Maniatis, T., E. F. Fritsch, J. Sambrook (1989) *Molecular Cloning: A Laboratory Manual,* 2d Edition, Cold Spring Harbor Laboratory, Cold Spring Harbor, N.Y. for details concerning selection markers for use in *E. coli.*

Proteins produced by prokaryotic cells may not necessarily fold properly. During purification from *E. coli,* the expressed protein may first be denatured and then renatured. This can be accomplished by solubilizing the bacterially produced protein in a chaotropic agent such as guanidine HCl and reducing all the cysteine residues with a reducing agent such as β-mercaptoethanol. The protein is then renatured, either by slow dialysis or by gel filtration. See U.S. Pat. No. 4,511,503.

Detection of the expressed protein is achieved by methods known in the art such as radioimmunoassay or Western blotting techniques or immunoprecipitation. Purification for *E. coli* can be achieved following procedures described in U.S. Pat. No. 4,511,503.

Expression in eukaryotes. A variety of eukaryotic expression systems such as yeast, insect cell lines, bird, fish, and mammalian cells, are known to those of ordinary skiil in the art. As explained briefly below, IA-2 or IA-2β proteins may be expressed in these eukaryotic systems.

Synthesis of heterologous proteins in yeast is well known. Sherman et al. (1982) *Methods in Yeast Genetics,* Cold Spring Harbor Laboratory, is a well-recognized work describing the various methods available to produce a protein in yeast.

Suitable vectors usually have expression control sequences, such as promoters, including 3-phosphoglycerate kinase or other glycolytic enzymes, and an origin of replication, termination sequences, and the like, as desired. For instance, suitable vectors are described in the literature (Botstein et al. [1979] *Gene* 8:17–24; Broach et al. [1979] *Gene* 8:121–133).

Two procedures are used in transforming yeast cells. In one case, yeast cells are first converted into protoplasts using zymolase, lytiacase, or glusulase, followed by addition of DNA and polyethylene glycol (PEG). The PEG-treated protoplasts are then regenerated in a 3% agar medium under selective conditions. Details of this procedure are given in the papers by Beggs, J. D. (9178) *Nature* 275:104–109 and Hinnen et al. (1987) *Proc. Natl. Acad. Sci. USA* 75:1929–1933. The second procedure does not involve removal of the cell wall. Instead, the cells are treated with lithium chloride or acetate and PEG and put on selective plates (Ito et al. [1983] *J. Bact.* 153:163–168).

IA-2 or IA-2β proteins, once expressed, can be isolated from yeast by lysing the cells and applying standard protein isolation techniques to the lysates. The monitoring of the purification process can be accomplished by using Western blot techniques or radioimmunoassay or other standard immunoassay techniques.

The sequences encoding IA-2 or IA-2β proteins can also be ligated to various expression vectors for use in transforming cell cultures of, for example, mammalian, insect, bird, or fish origin. Illustrative of cell cultures useful for the production of the polypeptides are mammalian cells. Mammalian cell systems often will be in the form of monolayers of cells though mammalian cell suspensions may also be used. A number of suitable host cell lines capable of expressing intact proteins have been developed in the art, and include the HEK293, BHK21, and CHO cell lines, and various human cells such as COS cell lines, HeLa cells, myeloma cell lines, Jurkat cells, etc. Expression vectors for these cells can include expression control sequences, such as an origin of replication, a promoter (e.g., the CMV promoter, a HSC tk promoter or pgk [phosphoglycerate kinase] promoter), an enhancer (Quenn et al. [1986] *Immunol. Rev.* 89:49), and necessary processing information sites, such as ribosome binding sites, RNA splice sites, polyadenylation sites (e.g., an SV40 large T ag ply A addition site), and transcriptional terminator sequences. Other animal cells useful for the production of proteins are available, for example, from the American Type Culture Collection Catalogue of Cell Lines and Hybridomas (7th Edition, 1992).

Appropriate vectors for expressing proteins in insect cells are usually derived from the SF9 baculovirus. Suitable insect cell lines include mosquito larvae, silkworm, armyworm, moth, and Drosophila cell lines such as a Schneider cell line (see Schneider, J. [1987] *Embryol. Exp. Morphol.* 27:353–365).

As indicated above, the vector, e.g., a plasmid, which is used to transform the host cell, preferably contains DNA sequences to initiate transcription and sequences to control the translation of the protein. These sequences are referred to as expression control sequences.

As with yeast, when higher animal host cells are employed, polyadenylation or transcription terminator sequences from known mammalian genes need to be incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague et al. [1983] *J. Virol.* 45:773–781).

Additionally, gene sequences to control replication in the host cell may be incorporated into the vector such as those found in bovine papilloma virus-type vectors. Saveria-Campo (1985) in *DNA Cloning, Vol. II, A Practical Approach,* D. M. Glover, ed., IRL Press, Arlington, Va., pp. 213–238.

The host cells are rendered competent or rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation and micro-injection of the DNA directly into the cells.

The transformed cells are cultured by means well known to one of ordinary skill in the art. Kuchler, R. J. (1977) *Biochemical Methods in Cell Culture and Virology,* Hutchinson and Ross, Inc. The expressed polypeptides are isolated from cells grown as suspensions or monolayers. The latter are recovered by well-known mechanical, chemical, or enzymatic means.

Following are examples which illustrate procedures, for practicing the invention. These examples should not be construed as limiting. All percentages are by weight and all solvent mixture proportions are by volume unless otherwise noted.

EXAMPLE 1

Evidence that Autoantibodies to IA-2 Occur in Patients with IDD

The intracellular (a.a. 603–979) and extracellular (a.a. 129–472) domains of IA-2 were expressed as fusion proteins with glutathione transferase (GST) from separate subclones in a pGEX bacterial expression vector. The cDNAs were verified by direct DNA sequencing, and the fusion proteins were induced by IPTG and purified by glutathione-agarose (Sigma). The fusion proteins were further processed by cleavage with human thrombin (Sigma) and the GST fusion partner removed by passage through a glutathione-agarose affinity column.

New Zealand rabbits were immunized against the extra and intra-cellular fragments of IA-2 to provide hyperimmune sera. An ELISA for IA-2 autoantibodies was developed as follows. Polyvinyl microtiter plates (Becton-Dickerson, Oxnard, Calif.) were coated with 0.4 $\mu g/100$ $\mu l$/well of the purified IA-2 fragments or GST expression proteins. The sera from 55 patients with IDD and 53 normal control persons were tested. Some 34% of the patients had IDD diagnosed within a year. One hundred $\mu g$ of the human sera was diluted 1:50 (IC domain) or 1:100 (EC domain) in BLOTTO-Tween (10 mM Tris-HCL, pH 8.0; 150 mM NaCl; 5% Carnation nonfat dry milk; 0.05% Tween 20; 0.05% $NaN_3$) and reacted with the antigens. The autoantibodies were in turn detected using a 1:2000 dilution of alkaline phosphatase labelled goat anti-human IgG (Southern Biotechnology Assoc. Birmingham Ala.) in BLOTTO-Tween. Polyacrylamide gel electrophoresis of the recombinant IA-2 fragments revealed bands of the predicted molecular weights, as confirmed by reactivity with the specific polyvalent rabbit antibodies, which also stained pancreatic islets. Of the patients, 21 reacted to the intracellular domain and 10 to the extracellular domain of IA-2, compared to 3 and 2 control sera respectively while 6 patients but only 1 control serum reacted to both fragments. Thus 25 patients (45.5%) had autoantibodies to the IA antigen overall, compared to only 4 controls (7.5%). Of the newly diagnosed patient group, 17 of 34 (50%) had IA-2 autoantibodies, while fewer (38.1%) had antibodies persisting beyond 1 year after diagnosis. Autoantibodies were also determined to $GAD_{65}$ produced by a baculoviral insect cell expression system, using a depletion ELISA assay (d-ELISA). Some 20 of the patients (37.7%) were found to be negative while all of the controls were negative. Strikingly, 21 of 29 IA-2 autoantibody negative patients (72%) were found to be $GAD_{65}$ autoantibody positive. Therefore, determination of both antibodies would correctly identify considerably more of the patients than would be possible by either antibody alone.

TABLE I

Reactivity of Sera From Diabetic Patients to IA-2 in Relationship to the Presence or Absence of Autoantibodies of $GAD_{65}$

| | | | IA-2 | | | |
|---|---|---|---|---|---|---|
| Diabetic Patients (n = 53) | | | Positive* | | Negative | |
| $GAD_{65}$ | n | % | n | % | n | % |
| Negative | 20 | 37.7 | 12 | 60 | 8 | 40 |
| Positive | 33 | 62.3 | 12 | 36 | 21 | 64 |

*-Samples with reactivity to the intracellular and/or extracellular domains of IA-2.

EXAMPLE 2

Evidence that IA-2 is a Major Autoantigen in IDD

Since IA-2 is an integral membrane protein expressed in its native state in restricted cell types in humans, the full length cDNA was next expressed in an eukaryotic rabbit reticulocyte transcription/translation system, and the recombinant protein radiolabelled with $S^{35}$ methionine was used to detect IA-2 autoantibodies by immunoprecipitation. The full length cDNA without its leader sequence was cloned into a pCR11 cloning vector (Invitrogen, San Diego Calif.) with a perfect Kozak translational start sequence (GCCGCCACC ATGG). One microgram of plasmid DNA was added to TNT coupled rabbit reticulocyte lysate system (Promega, Madison Wis.) in the presence of [$^{35}S$] methionine (Amersham, Arlington Heights, Ill.) at 30° C. for 2 hours. The translated reticulocyte lysate (at approximately 50,000–75,000 cpm) and 5 μl of each test serum was mixed in 100 μl of immmunoprecipitation buffer (20 mM Tris, pH 7.4, 150 mM NaCl and 1% Triton X-100). The reaction mixture was incubated overnight and 50 μl of 50% (v/v) protein A-agarose (Life Technologies, Gaithersburg, Md.) was added to the solution at 4° C. for one hour. After washing four times with immunoprecipitate buffer, the immunoprecipitation mixture was boiled in sample buffer and applied to an 8% SDS-PAGE gel. The gels were fixed with acetic acid/methanol (12.5%/12.5%) and then exposed to X-ray sensitive film overnight. The intensity of the IA-2 bands (approximately 106 kDa) was scored independently from 1–4+ by two independent investigators. One hundred coded sera comprising 50 from newly diagnosed patients and an equal number of matched controls were studied. Using this method, 66% of the patient sera but none of the controls were positive for autoantibodies to IA-2. Autoantibodies to $GAD_{65}$ were also performed by a D-ELISA method, and 52% were positive. In all, 86% of the patient sera but none of the controls were positive for autoantibodies to $GAD_{65}$ and/or IA-2, with 34% being positive to both antigens. There was an age-associated bias to the results. Of the patients diagnosed before age 20 years, 68% had IA-2 autoantibodies and 60% $GAD_{65}$ autoantibodies. However, of the patients diagnosed after age 20 years, only 46% were positive for IA-2 autoantibodies while 86% were positive for $GAD_{65}$ autoantibodies. These results were greatly improved from the earlier study using ELISA assays and IA-2 fragments. There are several possible explanations. It is probable that the disease associated autoantibodies react to the antigen through conformational epitopes. Thus reactivity may be greatly enhanced using the whole protein rather than its fragments. The method also involves antibody reactivities with the IA-2 protein in its native undenatured state, conditions which enhance reactions to conformational epitopes. Such is also the case for autoantibody reactivities to $GAD_{65}$.

EXAMPLE 3

Evidence that IA-2 and $GAD_{65}$ are Antigens that are Components of the ICA Reaction There was an excellent correlation between occurrence of autoantibodies either to IA-2 or $GAD_{65}$ and ICA, in that only one of 15 ICA positive sera that did not react to $GAD_{65}$ was not positive for IA-2 autoantibodies. This suggested that $GAD_{65}$ and IA-2 are component antigens of the ICA response. This conclusion is proven by an experiment in which 6 sera were selected because they were positive for ICA, and only $GAD_{65}$ (n=2) or only IA-2 (n=4) and subjected to absorption studies. Recombinant baculoviral expressed human $GAD_{65}$ was used to absorb out the corresponding autoantibody before the sera were applied to the ICA reaction. We found that this procedure reduced the ICA reactivity only of the sera which were found to be positive for $GAD_{65}$ autoantibodies, as expected from Atkinson et al. ([1993] *J. Clin. Invest.* 91:350–356). Conversely, we also absorbed out the 6 sera after passage through an IA-2 affinity column to remove autoantibodies to IA-2, before applying them to pancreatic sections for the ICA reaction, and found only those with autoantibodies to IA-2 to be reduced.

TABLE II

Absorption of ICA-Containing Sera with rIA-2 and $rGAD_{65}$

| Patient Serum | Reactivity of Sera With | | | Absorption of ICA-Containing Sera With rIA-2 Reactivity of Absorbed Sera with Islet Cells | $rGAD_{65}$ |
|---|---|---|---|---|---|
| | Islet Cells | rIA-2 | $rGAD_{65}$ | | |
| 1 | Pos | Pos | Neg | ↓↓ | — |
| 2 | Pos | Pos | Neg | ↓↓ | — |
| 3 | Pos | Pos | Neg | ↓ | — |
| 4 | Pos | Pos | Neg | ⊥ | ⊥ |
| 5 | Pos | Neg | Pos | — | ↓↓ |
| 6 | Pos | Neg | Pos | — | ↓↓ |

Reactivity of ICA-containing sera with islet cells as measured by intensity of immunofluorescence: greatly reduced (↓↓); reduced (↓); slightly reduced (⊥); no change (—).

These experiments document that $GAD_{65}$ and IA-2 are both antigens involved in the ICA response; however, some sera showed that double absorptions with both antigens did not ablate any of the ICA responses, suggesting that autoantibodies to additional autoantigen(s) must be often present in ICA positive sera. A candidate antigen is IA-2β. Preliminary data in fact suggests that more than 45% of sera from patients with IDD are autoantibody positive, compared to none of normal controls.

EXAMPLE 4

Evidence that Autoantibodies to IA-2 are Useful to Predict IDD

The human leukocyte antigens HLA-DR/DQ have been analyzed by a novel PCR based molecular typing system in more than 50 subjects with IDD. The high risk DRB1*03/DQB1*0201 and DRB1*04/DQB1*0302 haplotypes were over-represented in those positive for either autoantibodies to $GAD_{65}$ and/or IA-2. Thus, risk for IDD among patients and their relatives indicated a strong association between the IDD associated high risk HLA and appearance of these autoantibodies suggesting that the autoantibodies themselves would be expected to be associated with a high risk for IDD also.

In studies with 2500 normal school children and a similar number of first degree relatives of patients with IDD, we found that testing autoantibodies to IA-2, $GAD_{65}$, IAA and ICA, the combined predictive power of the IA-2 and $GAD_{65}$ test was greater than 90% in both groups for subsequent development of IDD.

EXAMPLE 5

Therapeutic Regimens

From the current disclosure and experimental results it is evident that IA-2 and IA-2β are major antigens in the pathogenesis of IDD, and are thus valuable in the diagnosis and therapy of the disease. Autoantibodies to these proteins are useful in disease prediction both in non-diabetic relatives of patients affected by IDD, as well as in the general population. Such autoantibodies may react mainly to determinants on the intracellular domain of IA-2 or IA-2β. Such antibodies will be detectable by radioimmunoassay using recombinant IA-2 or IA-2β depletion or D-ELISA and/or by ELISA or immunoprecipitation as outlined here. Based upon experience of the inventors with $GAD_{65}$ and insulin autoantibody analyses, baculoviral based eukaryotic expression systems are likely to be preferred to fold the protein appropriately, and glycosylate the protein if this enhances the antibody binding ability. However, such expression systems as COS cells, yeast cells, and bacterial cells such as E. Coli could be used for this purpose as those skilled in the art are readily able to appreciate.

Fluid-based immunoassays using the antigens and antibodies of this invention provide the greatest sensitivity to the method since autoantibodies of relevance mostly react to their respective autoantigen through conformational rather than through linear epitopes. The RIA and d-ELISA methods are most useful in fulfilling these properties. Accordingly, autoantibodies to human $GAD_{65}$, IA-2, and IA-2β antigens can replace the ICA method for prediction of IDD, with chemically based assays giving greater precision, reproducibility, and specificity without compromising sensitivity or positive predictive power.

Cellular responses, such as by proliferation or by cytokine elaboration after in vitro exposure to IA-2 or IA-2β are also useful in disease prediction.

The IA-2 or IA-2β molecule or peptide derivatives of IA-2 or IA-2β are used in antigen based therapies, including giving the antigens intravenously to induce anergy; deliberately immunizing against the antigen such as to induce an antibody response mediated by T helper-2 type lymphocytes to induce immunosuppressive effects on the pathogenic T helper-1 lymphocyte subset; or orally fed antigen such as to induce anergy and suppressive effects. Intravenous $GAD_{65}$ antigens have been given in early life in NOD mice and shown to induce reductions in the degree of the inflammatory infiltrates or insulitis lesions and prevent the onset of hyperglycemia (Kauffman et al. [1994] Nature 366:69–72). Subcutaneous immunizations by insulin and insulin B chains in incomplete Freund's adjuvant will prevent diabetes in NOD mice for prolonged periods without reductions in the insulitis lesions. The infiltrating cells however change their phenotype from ones that make large amounts of interferon gamma to ones that do not. Transfer of splenic lymphocytes from mice protected from diabetes in this way also convey protection for periods of up to a month. The intervention thus induces an active immunosuppressive effect and an insulitis lesion that is protective rather than destructive associated with a switch from Th1 to Th2 responses. Further, the effect must be beyond that merely involving autoimmunity to insulin, since beta cell destruction is arrested. The release of protective cytokines into the milieux of the islet must then also inhibit adjacent autoimmunity responses to other self-antigens through a bystander effect (Muir, Maclaren et al. [1995] J. Clin. Invest. 95:628–634; Ramiya, Muir, Maclaren [1995] Clin. Immunotherapy 3:177–183.) Repeated feedings of defined autoantigens may also be used to inhibit ongoing autoimmune diseases. In the case of the NOD mice, this has occurred through orally administered insulin (Weiner et al. [1991] Proc. Natl. Acad. Sci USA 88:10252–10256) as well as through the use of oral feedings of insulin and GAD (Muir, Maclaren et al. [1994] Diabetes/Metabolism Reviews 9:279–287). Accordingly, therapeutic methods employing IA-2 or IA-2β alone or in combination with other antigens, improves the therapeutic efficacy of such treatments by providing an additional component of the ICA reaction.

EXAMPLE 6

Collection of Biological Fluid for Detection of Autoantibodies

A volume of greater than 500 microliters of whole blood is collected from the individual to be tested for IA-2 or IA-2β autoantibodies. The blood is drawn into a glass vacutainer tube directly, or into a syringe followed by transfer into a glass vacutainer tube. In order to obtain sera (blood devoid of clotting factors), the common vacutainer tubes used are termed a red top tube (devoid of sodium heparin), or a serum separator (STS) tube. If a common red top tube is used, the tube is allowed to clot (a period of greater than 10 minutes), and the clot removed. At this period of time, either sample tube may be centrifuged for 5 minutes at 1000 rpm at room temperature. The serum within the sample is removed and placed into a plastic storage vial and sealed tightly. The sample can be frozen at −20° until IA-2 or IA-2β autoantibody analysis.

EXAMPLE 7

Methods of Detecting IA-2 or IA-2β Antibodies

In addition to the use of immunoprecipitation techniques, the subject invention can be practiced utilizing any other procedures which facilitate detecting the presence of antibodies to IA-2 or IA-2β. For example, other immunological methods which can be used include enzyme linked immunosorbent assay (ELISA) and radioimmunoassay (RIA). The principles and experimental methods of these procedures are well known to those skilled in the art. The assays can be carried out rapidly and efficiently by the use of natural or recombinant proteins which bind with the antibodies to IA-2 or IA-2β. Both whole cell and cell lysate procedures are familiar to those working in this field and can be readily employed to detect the IA-2 or IA-2β antibodies.

The amino acid sequences of IA-2 and IA-6β can be analyzed to ascertain immunologically reactive epitopes. These epitopes are amino acid sequences which will react immunologically with the antibodies to IA-2 or IA-2β. These sequences can then be produced recombinantly. For recombinant production, the DNA coding for the epitopes is inserted into a vector which is then used to transform an appropriate host cell to express the desired amino acid sequence. Although bacteria, insects, yeasts, and mammalian cells could all serve as appropriate hosts, if protein folding is an important factor in the reactivity of the epitope, then an eukaryotic cell would be a preferred host.

Purified protein or lysate of the cells producing the protein could be used for the assays.

Also, an alternative to using IA-2 or IA-2β antigens would be to use antibodies generated to IA-2 or IA-2β, otherwise known as an anti-antibody. This antibody would immunoprecipitate with IA-2 or IA-2β and the detection could be carried out as described above.

EXAMPLE 8

Treatment of IDD

The specific event or agent which triggers the onset of diabetes has not been identified. A virus carrying an antigen similar to the IA-2 or IA-2β protein may provoke both a normal immune response to the virus and also an abnormal, autoimmune response to IA-2 or IA-2β through its molecular mimicry with the viral proteins. The genetic susceptibility is thus expressed by an exaggerated or prolonged immune response to the environmental agent which initiates the disease process. It is also possible that the IA-2 or IA-2β protein may have a delayed expression in the development of islet cells in ontogeny, rendering it antigenic because tolerance to it would not have been developed in the early stages of life.

A novel therapy of the subject invention involves the injection into the bloodstream of a toxin bound to a purified form of the IA-2 or IA-2β antigen. The antigen-toxin complex would quickly reach the lymph nodes where it is taken up by immune cells that normally produce the antibodies to IA-2 or IA-2β. Also, the antigen-toxin complex would be bound by the T-lymphocytes that recognize the antigens on β-cells. Thus, the specific immune cells involved in β-cell destruction are poisoned and inactivated, leaving non-destructive immune cells unharmed. The hybrid protein could comprise, for example, a diphtheria toxin joined together with the IA-2 or IA-2β antigen. The construction of such a hybrid toxin could proceed, for example, according to the disclosure of U.S. Pat. No. 4,675,382 (Murphy) relating to hybrid proteins.

In a preferred method of the subject invention, prevention or treatment involves the administration of autoantigens to the susceptible individual. IDD has an autoimmune etiopathogenesis, as discussed above. Various mechanisms have been proposed that would account for the beneficial value of administering autoantigens as a preventive treatment. In addition, it is also well known in the art that the administration of autoantigens can be used to induce immunological non-responsiveness, that is, specific tolerance of the antigen. See U.S. Patent No. 5,114,844; Nagler-Anderson et al. (1986) *Proc. Natl. Acad. Sci USA* 83:7443–7446; Miller et al. (1984) *Clin. Immunol. Immunopathol.* 31:231–240; Silverman et al. (1983) *J. Immunol.* 131:2651–2661; Michael (1989) *Immune Invest.* 18:1049–1054. The administration of the IA-2 or IA-2β antigens according to the subject invention can be done using procedures, formulations, and administration routes well known in the art. As one skilled in the art having the benefit of this disclosure would appreciate, the administration of the IA-2 or IA-2β protein or peptide can be by, for example, parenteral, oral, intranasal, or by modification of the patient's genome to express an antigenic epitope.

EXAMPLE 9

Use of IA-2 Antibodies in Conjunction with Pancreas Transplantation

One approach for treatment of a patient with IDD is to transplant normal islets as replacements for the damaged or destroyed β-cells. Segmental and whole pancreas transplantations have been performed successfully in a number of patients with diabetes. However, permanent immunosuppressive therapy is required to maintain the grafts and prevent rejection. Segmental or whole pancreas transplants under continuous immunosuppressive therapy have produced normal levels of blood glucose in some patients with diabetes. Pancreatic transplants are done late in the course of diabetes and will probably not reverse complications such as nephropathy and indeed may worsen retinopathy.

Importantly, successful pancreatic grafts between identical twins have been maintained without immunosuppressors; however, autoimmune islet cell destruction has occurred with recurrence of diabetes. Thus, even when the graft is not rejected, there is obligatory need for immunotherapies to prevent disease recurrence. The destruction (rejection) of transplanted islets may be due, at least in part, to the re-presentation of autoantigens responsible for the autoimmune destruction. There is no specific immunotherapy to prevent the autoimmune destruction (rejection of transplanted islets/pancreas) at present. In order to prevent the autoimmune destruction of either transplanted islet cells or pancreas, a specific immunotherapy using a hybrid toxin or tolerance strategy, as detailed above, can be used to prevent islet cell destruction. The combined use of the immunotherapies could make islet cell/pancreas transplantation a therapeutic tool for the treatment of IDD.

EXAMPLE 10

Kits for Assay of IA-2 or IA-2β Autoantibodies and IDD

A reagent kit can be provided which facilitates convenient analysis of serum samples using the novel procedures described here. Kits can be prepared which utilize recombinant or synthetically produced intact IA-2 or IA-2β protein (s) or immunoreactive peptides to serve as an antigen for the detection of antibodies to IA-2 or IA-2β. Alternatively, antibodies specifically developed to detect antibodies to IA-2 or IA-2β may also be useful. The principles and methods for ELISA and RIA technologies to detect antibodies are well-established.

As an example, for the ELISA assay, one such kit could comprise the following components:

1. IA-2 protein, peptide, or antibodies to IA-2 antibodies;
 2. Enzyme (e.g., peroxidase);
 3. Conjugated animal anti-human immunoglobulin; and
 4. Positive and negative controls.

The above kit could be modified to include 96 well plastic plates, calorimetric reagents, ELISA readers, blocking reagents, and wash buffers. Inclusion of $GAD_{65}$ antigen would also be highly preferred.

Also by way of example, for the RIA, one such kit could comprise the following components:

1. Radiolabeled IA-2 protein(s), peptide, or antibodies to IA-2 antibodies;
 2. Wash buffers;
 3. Polyethylene glycol (PEG);
 4. Goat or sheep antihuman precipitating (second) antibodies; and
 5. Positive and negative controls.

Either of the above kits may be modified to include any appropriate laboratory supplies or to exclude non-essential compounds such as the buffers, PEG, or controls. Presence of IA-2 autoantibodies as detected by using this kit is indicative of IDD or susceptibility to IDD, especially if in addition, $GAD_{65}$ reactive autoantibodies are detected. To preserve the conformational epitopes in their reactivities to their respective autoantibodies, the results of a ligand phase antibody reaction can be determined by measurement of the remaining antigens by an ELISA Analogous kits can be prepared using IA-2β.

EXAMPLE 11

Cloning and Sequencing of Mouse IA-2β cDNA Clones

Twenty-one different members of the protein tyrosine phosphatase (PTP) family were identified from short nucleotide sequences isolated from a polymerase chain reaction (PCR) amplified cDNA library which was constructed with cDNAs reverse transcribed from pancreatic beta cells and a pair of degenerate primers derived from known PTP nucleotide sequences. Three of these 21 PTPs were previously unknown. One of them is referred to herein as IA-2β. A 300 bp fragment of IA-2β isolated from the PCR-based PTP library was used as a probe to screen a mouse neonatal brain lambda ZAPII cDNA library (Stratagene, La Jolla, Calif.).

Two clones extending approximately 2 kb upstream from the polyA tail were isolated by screening 400,000 plaques. The insert of the longer clone was used to re-screen the same library. Seven additional cDNA clones were obtained that contained sequences overlapping with original clones. The nine different cDNA clones were isolated and their nucleotide sequences were determined by double strand sequencing by the chain termination method using sequenase version 2.0 sequencing kit (U.S. Biochemical Corporation, Cleveland, Ohio). The insert sizes ranged from 0.6 kb to 2.5 kb and the total overlapped sequence was approximately 3.5 kb. Comparison of the nucleotide sequence of the different clones revealed that the 3'-untranslated region of some of the clones lacked a stretch of 306 bp, perhaps the result of alternative splicing. A compressed GA-rich stretch at the 3'-end of the untranslated region further hampered resolution of the exact sequence. Nonetheless, all nine cDNA clones possessed the same open reading frame that translated into a protein of 723 amino acids with an intracellular, transmembrane and extracellular domain (FIG. 1). Sequence analysis using the GenBank database showed that IA-2β is a member of the transmembrane PTP family. Its intracellular segment contains a single PTP domain which shows 74% identity to IA-2. The PTP core sequence of IA-2β (VHCSDGAGRS/TG) differs from that of IA-2 by only one amino acid. In contrast, the partial extracellular sequence of IA-2β shows only 26% identity with the extracellular domain of IA-2.

EXAMPLE 12

Northern Analysis

Total RNAs were isolated from normal mouse tissues and tumor cell lines, αTC-1 and βTC-1, by the acid guanidinium thiocyanate/phenol/chloroform extraction method (Chomczynski, P., N. Scchi [1987] *Anal. Biochem.* 162:156–159). RNA samples (20 μg each) were electrophoresed in a 1% agarose/5.4% formaldehyde gel, transferred to nitrocellulose membrane (Schleicher & Schuell, Keene, WH) via capillary blotting. Hybridization was performed as described previously (Lan, M. S., J. Lu, Y. Goto, A. L. Notkins [1994] *DNA and Cell Biology* 13:505–514). IA-2β cDNA S (a.a. 3 to a.a. 470) void of PTP domain or full-length IA-2 cDNA were used as the probe for Northern analysis. Ribosomal RNAs were used to verify the quality of RNAs.

Since the intracellular domain of IA-2β shows high similarity to the intracellular domain of IA-2, Northern analysis was performed using as the probe a $^{32}$P-labeled IA-2β sequence void of the PTP domain. FIG. 2A shows that a 5.5 kb mRNA band was prominent in the insulinoma cell line, βTC-1 and brain, less prominent in the glucagonoma cell line, αTC-1, pancreas and stomach, and barely detectable in colon. The other tissues tested including thymus, ovary, muscle, skin, heart, kidney, spleen, and liver were negative. For comparison, Northern analysis was performed on αTC-1 and βTC-1 cells with a $^{32}$P-labeled IA-2 sequence as the probe. FIG. 2B shows that a 3.8 kb mRNA band was very prominent in αTC-1 cells, but less prominent in βTC-1 cells. A weaker signal of larger message was detected in αTC-1 cells that may be the result of alternative splicing. Because of its sequence similarity with IA-2 and strong expression in βTC-1 cells, we refer to this new cDNA as IA-2β.

EXAMPLE 13

Radioimmunoprecipitation of In Vitro-Translated Intracellular Domain of IA-2β Autoantigen with IDD Sera and Competitive Immunoprecipitation The intracellular domain of mouse IA-2β cDNA (aa. 345 to a.a. 732) was PCR amplified with a perfect Kozak translational start sequence (GCCGCCACCATGG) that was engineered at the 5'-end of the sequence (Kozak, M. [1987] *Nucl. Acids Res.* 15:8125–8148) and subcloned into a pCRII cloning vector (Invitrogen, San Diego, Calif.). Polymerase chain reaction (PCR) was performed with 10 ng of IA-2β cDNA as template. The PCR conditions were as follow: 1 minute at 94° C., 1 minute at 55° C., 1.5 minutes at 72° C. for 35 cycles. A similar strategy, with a perfect Kozak sequence, was employed to clone the intracellular domain of mIA-2 (a.a. 598 to a.a. 979). The in vitro transcription/translation product (41 kDa) was prepared with 1 μg of plasmid DNA in a TNT coupled rabbit reticulocyte lysate system (Promega, Madison, Wis.) in the presence of [$^{35}$S] methionine (Amersham, Arlington Heights, Ill.) at 30° C. for 2 hours. Radiolabeled protein was determined by 10% trichloroacetic acid precipitation. Immunoprecipitation was performed as described below. Translated reticulocyte lysate (approximately 50,000–75,000 cpm) and 5 μl of tested serum were mixed in 100 μl of immunoprecipitation buffer (20 mM Tris, pH 7.4, 150 mM NaCl, and 1% Triton X-100). The reaction mixture was incubated overnight at 4° C. and 50 μl of 50% (v/v) Protein A-Agarose (Life Technologies, Gaithersburg, Md.) was added to the solution at 4° C. for one hour. The immunoprecipitation mixture was washed four times with immunoprecipitation buffer, boiled in sample buffer and applied to 10% SDS-PAGE gel. The intensity of the IA-2β band (approximately 41 kDa) was scored from 1+ to 4+ by two independent investigators.

Human subjects. Fifty newly onset IDD patients who had been diagnosed within a week of their blood sampling and 50 age-matched controls with no history of autoimmune disease, were studied. Blood samples were collected under informed consent as approved by the University of Florida Institutional Review Board.

Preparation of rabbit hyperimmune serum and mouse monoclonal antibody. Rabbit polyclonal antisera were prepared against the intracellular PTP domain of the IA-2 molecule by immunizing two male New Zealand White rabbit with multiple subcutaneous injections at the back of 125 μg of bacterial expressed GST-IA-2 fusion protein emulsified in incomplete Freund's adjuvant. Injections were performed every two weeks. Serum was collected and tested for immunoreactivity with bacterial expressed fusion protein. Mouse monoclonal antibody, IA-2/161, was prepared against the PTP domain of the IA-2 molecule by conventional hybridoma technology.

Figure 3:
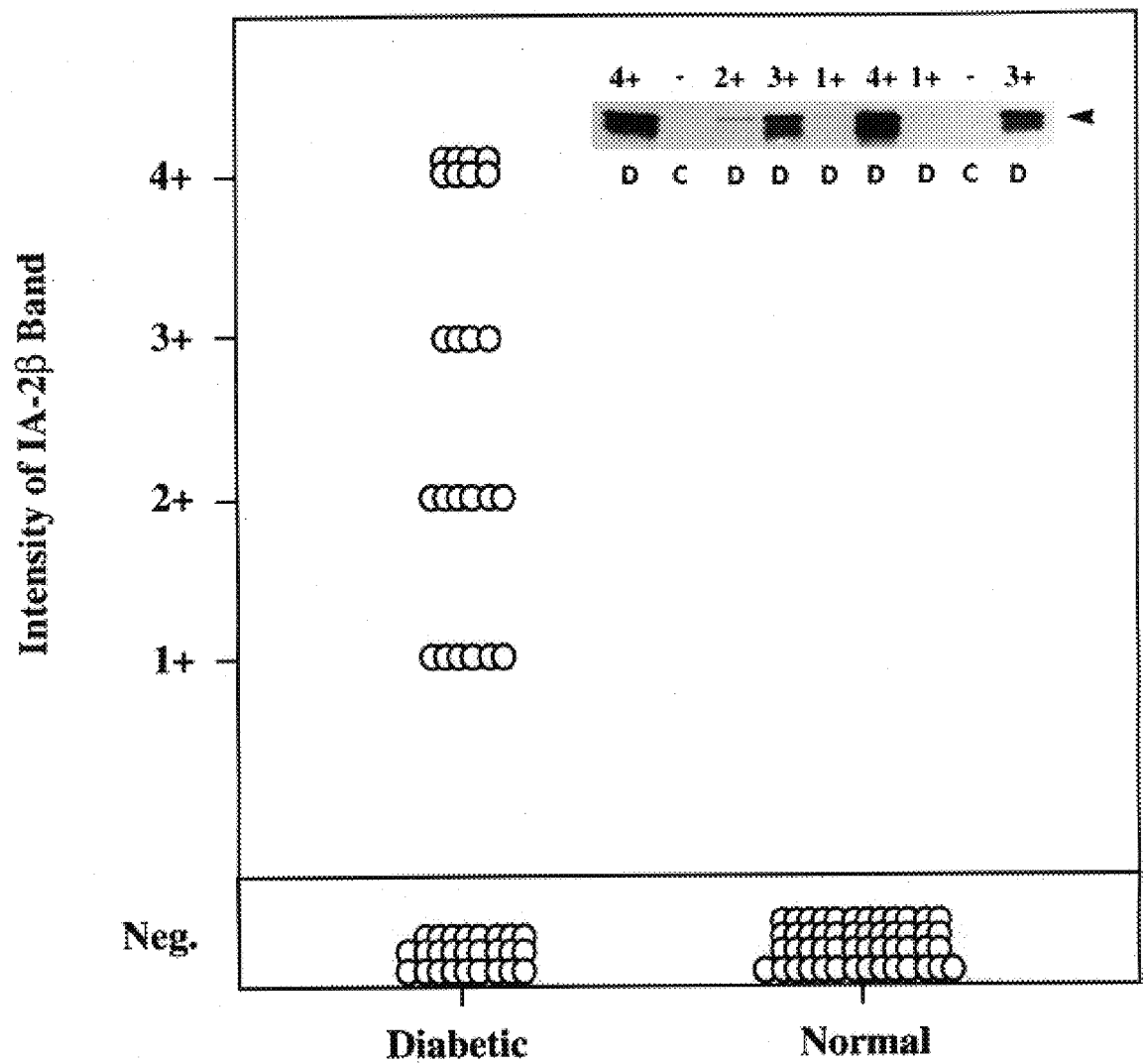
FIG. 3. Sera from 50 patients with clinically documented IDD and 50 normal controls were tested for autoantibodies to the intracellular domain of murine IA-2β by radioimmunoprecipitation. The intensity of bands with a molecular weight of 41 kDa were scored on a 1+ to 4+ scale. Representative sera with different band-intensities are illustrated in the insert. Diabetic sera (D), control sera (C).

Radiolabeled IA-2β then was immunoprecipitated with serum from IDD patients and separated on a 10% SDS-PAGE gel. The insert in FIG. 3 shows seven representative sera from IDD patients that recognized the in vitro translated product. The intensity of the bands ranged from 1+ to 4+.

Fifty coded sera from diabetic patients and 50 coded sera from controls then were tested by radioimmunoprecipitation for autoantibodies to the IA-2β intracellular domain. As seen in FIG. 3, 46% of the sera from IDD patients, but none of the sera from controls, reacted with IA-2β.

EXAMPLE 14

Immunoprecipitation and Blocking of 37/40 Tryptic Fragments from IA-2β/IA-2 Autoantigens A mouse insulinoma cell line, βTC-1, and a mouse glucagonoma cell line, αTC-1, were maintained at low glucose DMEM medium supplemented with 10% fetal calf serum. Before labeling, a 70% confluent culture was incubated in methionine-free medium supplemented with 10% dialysed fetal calf serum for 1 hour to deplete the intracellular methionine pool. The culture was subsequently added $^{35}$S-methionine (100 μCi/ml) for 5 hours. The labeled cells were harvested and prepared for membrane fraction as described (Christie, M. R., et al., 1990, supra). Radiolabeled cell lysates (1×10$^7$ cpm) were precipitated with diabetic serum for overnight and co-precipitated by Protein A-Agarose beads. After being washed three times with precipitation buffer, the beads were washed with water once and incubated with trypsin (50 or 100 μg/ml) on ice for 20 minutes. The precipitate was washed once again with water, boiled in 1× SDS sample buffer and separated on a 10% SDS-PAGE gel. Blocking reaction was performed by pre-incubation of the serum with rabbit reticulocyte lysate containing unlabeled intracellular domain of IA-2 (a.a. 598 to 979) or IA-2β (a.a. 354 to 723), translated into 42 kDa and 41 kDa products respectively, for 2 hours. Radiolabeled cell lysate was added, precipitated and trypsinized as described above. Labeled reticulocyte lysates of full-length IA-2, intracellular domain of IA-2 and IA-2β were also directly treated with trypsin (50 μg/ml) on ice for 20 minutes before loading on a 10% SDS-PAGE gel.

Figure 4A:
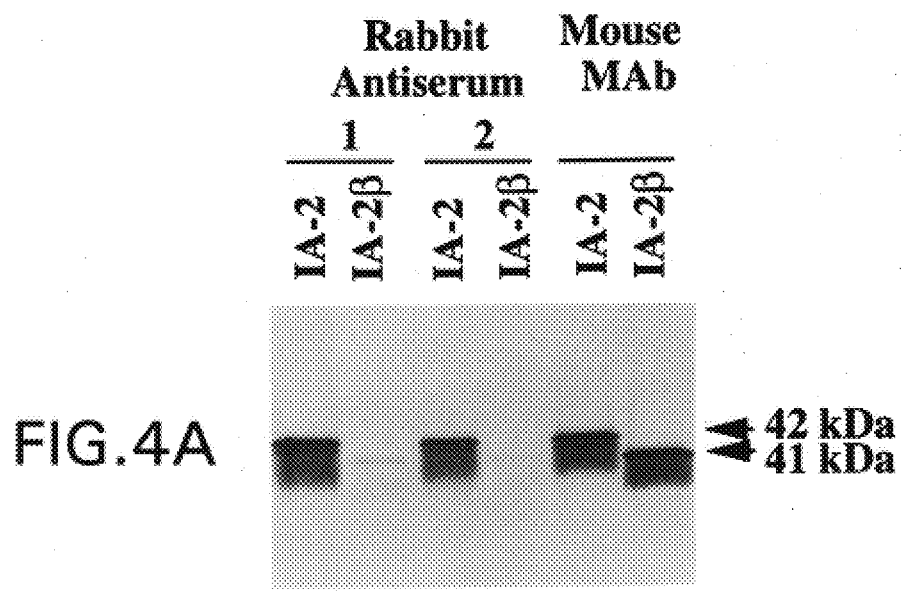
FIGS. 4A–4B. Competitive radioimmunoprecipitation.
Figure 4B:
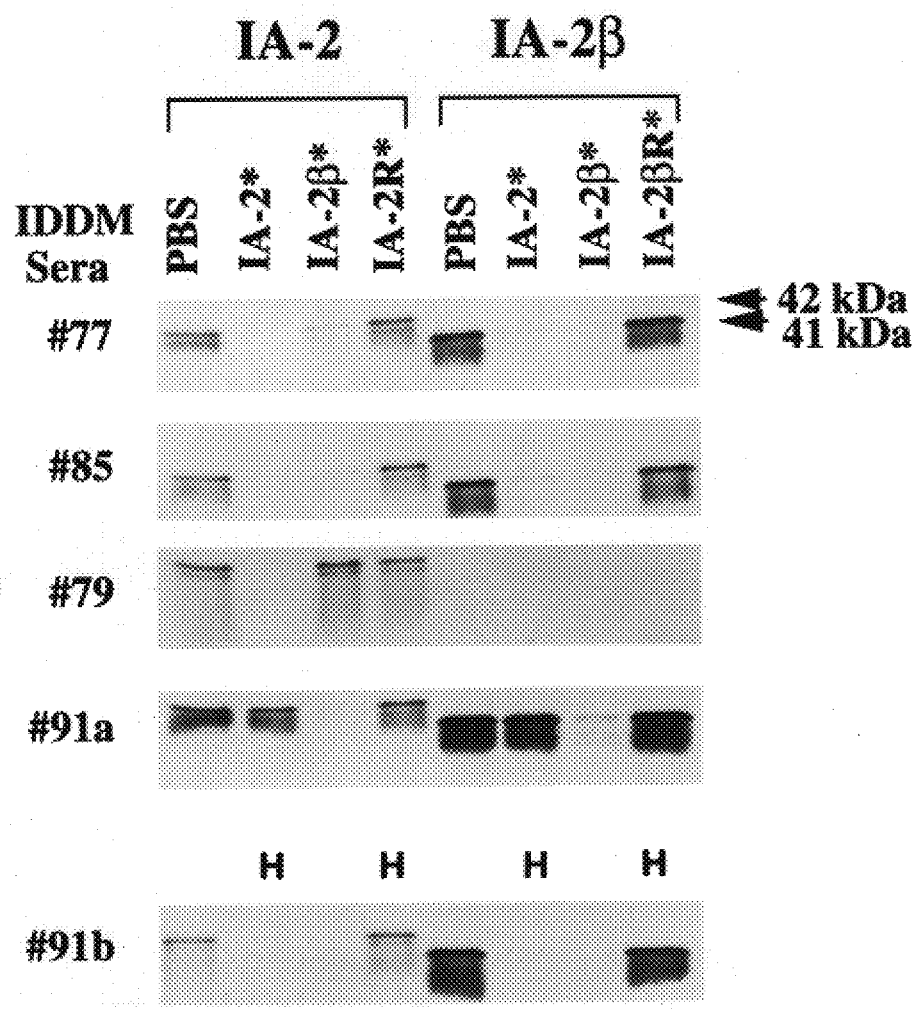

As seen in FIG. 4A, hyperimmune rabbit sera and mouse monoclonal antibody to the intracellular domain of IA-2 reacted not only with IA-2, but also with IA-2β, precipitating a 42 kDa and 41 kDa protein, respectively. The difference in the intensity of the reactivity of the rabbit hyperimmune sera with IA-2 and IA-2β may reflect a difference in the epitopes recognized on these two molecules. Sera from diabetic patients (#77 and #85) recognized and precipitated radiolabeled IA-2 and IA-2β and both unlabeled IA-2 and IA-2β blocked this precipitation (FIG. 4B). Some diabetic sera (e.g., #91a) that recognized both IA-2 and IA-2β could be blocked by 10-fold excess of unlabeled IA-2β (as compared to radiolabeled antigen), but not by the same concentration of IA-2. Higher concentrations of unlabeled IA-2 (50-fold excess) were required for blocking the same serum (e.g. #91b), arguing that the autoantibodies in this serum have a higher affinity for and/or recognize predominantly the IA-2β epitopes. Still other diabetic sera (e.g., #79) recognized only IA-2, and the reaction could be blocked by IA-2, but not by IA-2β. Taken together, these studies show that autoantibodies to IA-2 and IA-2β have a high degree of cross-reactivity, but that both common and distinct epitopes are present on these molecules.

Figure 5:
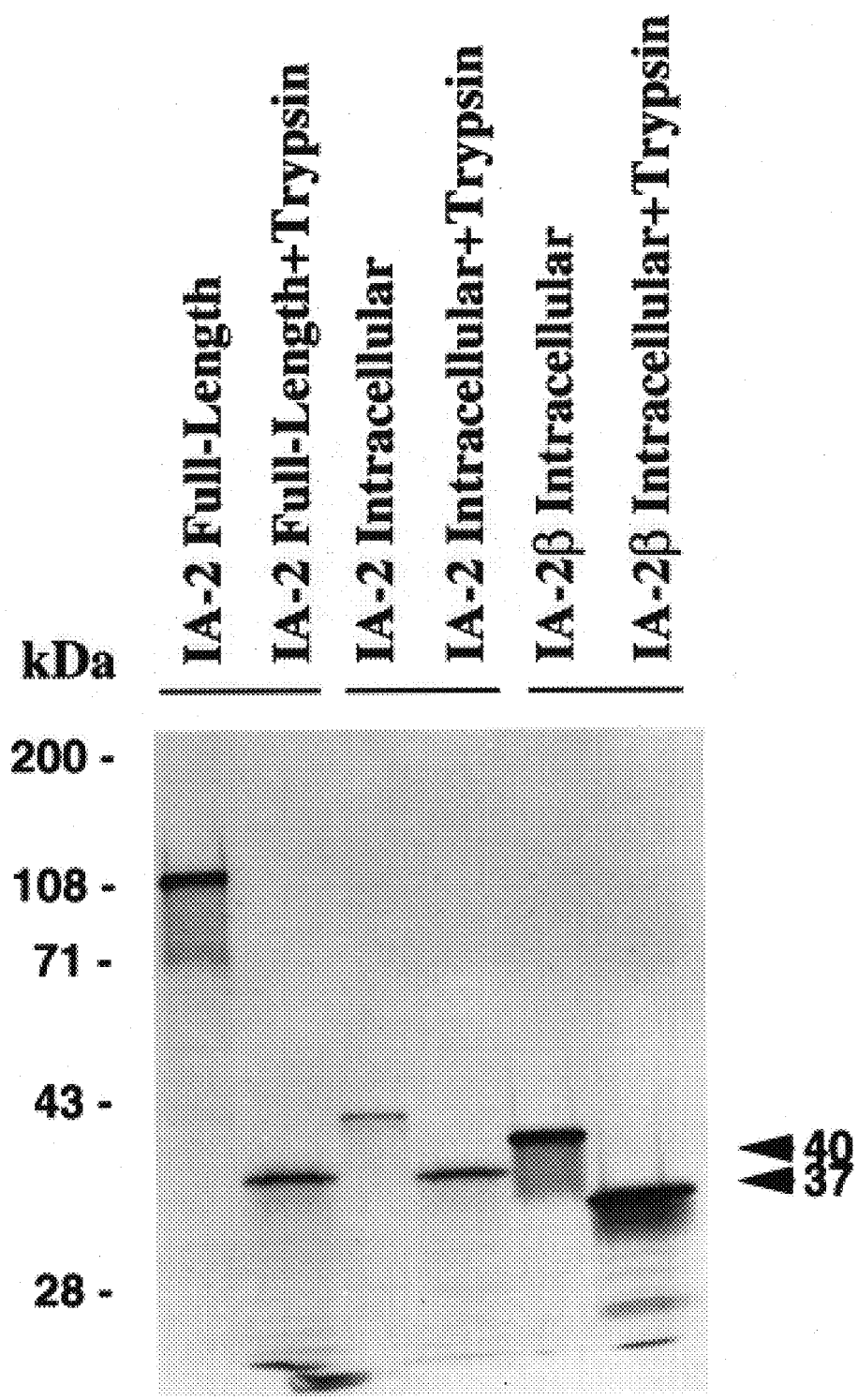
FIG. 5. Trypsin treatment converts IA-2 and IA-2β into 40 and 37 kDa fragments, respectively. In vitro translated full-length IA-2 (lanes 1 and 2), intracellular domain of IA-2 (lanes 3 and 4) and IA-2β (lanes 5 and 6) were trypsinized (50 μg/ml) before electrophoresis on a 10% SDS-PAGE gel.

Trypsin treatment converts IA-2β and IA2 into 37 and 40 kDa fragments. The in vitro translated products of full-length IA-2 (106 kDa) and intracellular IA-2 (42 kDa) were subjected to trypsin treatment. As seen in FIG. 5, the predominant tryptic fragment migrated as a 40 kDa band. In contrast, the tryptic fragment of intracellular domain of IA-2β (41 kDa) migrated as a 37 kDa band. Both tryptic fragments could be precipitated by diabetic sera.

Figure 6A:
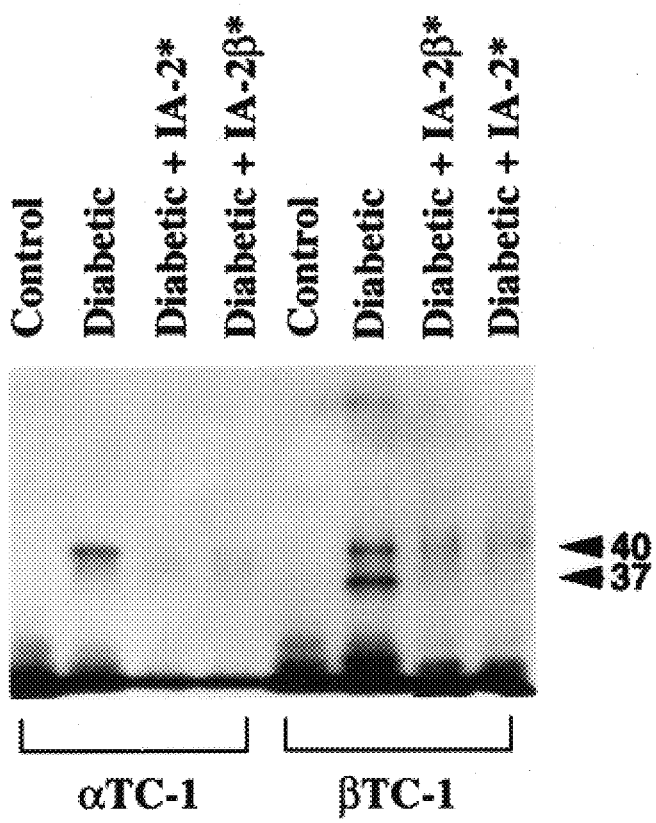
FIGS. 6A–6B. Blocking of 37/40 kDa tryptic fragments by unlabeled (*) recombinant intracellular domains of IA-2β and/or IA-2. In vitro radiolabeled preparations of αTC-1 and βTC-1 lysates (1×10$^7$ cpm) were immunoprecipitated with control or diabetic sera from two different patients (FIG. 6A and FIG. 6B). Precipitates were treated with trypsin (100 μg/ml) before loading onto a 10% SDS-PAGE gel. Blocking reactions were performed by incubating IDD sera for 2 hours with the unlabeled recombinant intracellular domain of IA-2 or IA-2β before adding the radiolabeled lysate from αTC-1 and βTC-1 cells.
Figure 6B:
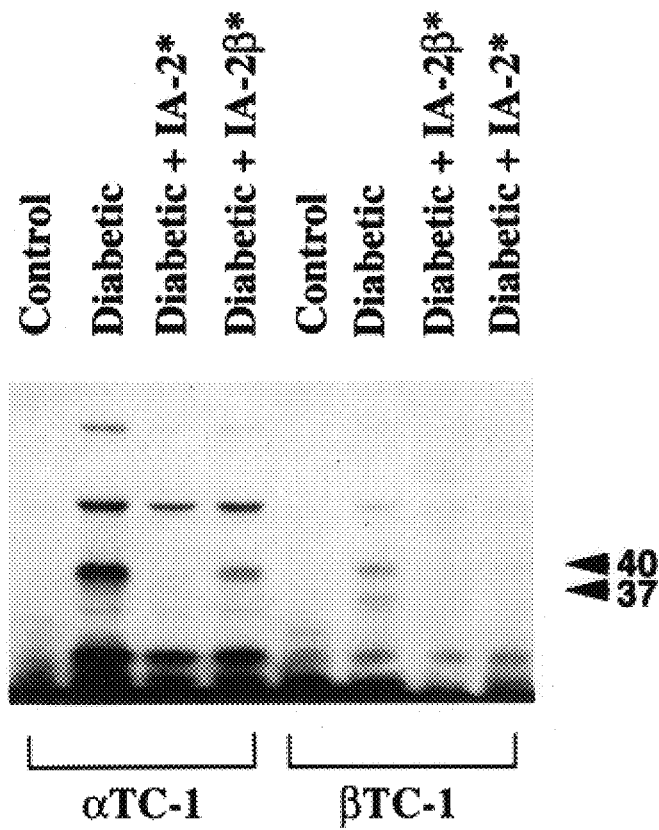

Blocking of 37/40 kDa tryptic fragments from islet cells by intracellular domain of IA-2β and/or IA-2. To further show that the 37 and 40 kDa tryptic fragments were derived from IA-2β and IA-2, tryptic fragments from αTC-1 and βTC-1 cell lines were precipitated with diabetic sera. As seen in FIGS. 6A–6B, diabetic sera precipitated only a 40 kDa band from αTC-1 cells and a 37/40 kDa doublet from βTC-1 cells. These findings are consistent with the relative abundance of IA-2 mRNA in αTC-1 and IA-2β mRNA in βTC-1 cells (FIGS. 2A–2B). Blocking experiments (FIG. 6A) showed that both unlabeled recombinant IA-2 and IA-2β were capable of preventing the precipitation of radiolabeled IA-2 and IA-2β by diabetic sera from patient A Similarly, unlabeled recombinant IA-2 completely blocked the precipitation of radiolabeled IA-2 by diabetic serum from patient B, but unlabeled recombinant IA-2β was somewhat less effective (e.g., αTC-1 cells) (FIG. 6B). This may be due to the different epitopes recognized on IA-2 and IA-2β molecules by sera from different diabetic patients.

EXAMPLE 15

Cloning of the Human IA-2β

The mouse cDNA (4 kb) was used as a probe to screen a human brain cDNA library. Several clones were identified and sequenced. Among the clones identified, there were different sized versions. Close to the N-terminus of the longer version there are an additional 51 nucleotides as compared to other clones (the shorter version). The additional 51 nucleotides gives rise to an additional 17 amino acids in the longer version.

EXAMPLE 16

Use of IA-2α in Diagnosis, Therapy and Prophylaxis of Diabetes

All of the techniques and methods for using IA-2 disclosed herein, including the detection methods, prophylactic and therapeutic methods and diagnostic kits are directly applicable for use with IA-2β.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A composition comprising an isolated mammalian IA-2β polypeptide that specifically binds to islet cell autoantibodies and said IA-2β polypeptide has the sequence shown in SEQ ID NO:3.

2. The composition of claim 1 which further comprises an isolated $GAD_{65}$ molecule, an isolated IA-2 molecule or both.

3. An isolated IA-2β polypeptide that specifically binds to islet cell autoantibodies and said IA-2β polypeptide has the sequence shown in SEQ ID NO:3.

4. An isolated IA-2β polypeptide consisting of the sequence of SEQ ID NO. 1, SEQ ID No. 3 or SEQ ID NO.5.

5. The composition of claim 2, which further comprises insulin.

6. A fragment of an isolated mammalian IA-2β polypeptide of claim 3 comprising an intracellular domain of IA-2β as shown in SEQ ID NO:1, wherein the fragment specifically binds to islet cell autoantibodies.

* * * * *

UNITED STATES PATENT AND TRADEMARK OFFICE
CERTIFICATE OF CORRECTION

PATENT NO. : 5,989,551
DATED : November 23, 1999
INVENTOR(S) : Maclaren et al.

It is certified that error appears in the above-identified patent and that said Letters Patent is hereby corrected as shown below:

Columns 27 - 28,
SEQ ID NO:1, section (vi), (C) after "INDIVIDUAL ISOLATE:", delete "Human IL-2" and insert therefor -- Human IA-2 --.

Columns 31 - 32,
SEQ ID NO:2, section (vi), (C) after "INDIVIDUAL ISOLATE:", delete "Human IL-2" and insert therefor -- Human IA-2 --.

Columns 35 - 36,
SEQ ID NO:3, section (vi), (C) after "INDIVIDUAL ISOLATE:", delete "Human IL-2" and insert therefor -- Human IA-2 --.

Columns 39 - 40,
SEQ ID NO:4, section (vi), (C) after "INDIVIDUAL ISOLATE:", delete "Human IL-2" and insert therefor -- Human IA-2 --.

Signed and Sealed this

Sixteenth Day of April, 2002

*Attest:*

JAMES E. ROGAN
*Attesting Officer*  Director of the United States Patent and Trademark Office